Figure 1E:
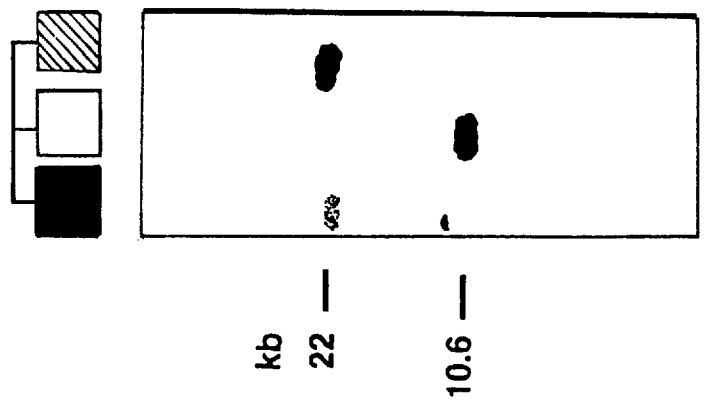

United States Patent [19]
Mandel et al.

[11] Patent Number: 5,869,039
[45] Date of Patent: Feb. 9, 1999

[54] X-LINKED ADRENOLEUKODYSTROPHY GENE AND CORRESPONDING PROTEIN

[75] Inventors: Jean-Louis Mandel, Schiltigheim; Patrick Aubourg, Sceaux; Jean Mosser; Claude Sarde, both of Strasbourg, all of France

[73] Assignee: Institut National de la Sante et de la Recherche Medicale, Paris Cedex, France

[21] Appl. No.: 479,403

[22] Filed: Jun. 7, 1995

Related U.S. Application Data

[62] Division of Ser. No. 136,277, Oct. 15, 1993, Pat. No. 5,644,045.

[51] Int. Cl.[6] .......................... A01N 63/00; A61K 48/00
[52] U.S. Cl. ................................ 424/93.21; 435/172.3; 435/320.1; 435/375; 935/62
[58] Field of Search .............. 514/44; 536/23.5, 536/23.2; 435/320.1, 172.3, 375; 424/93.21; 935/62

[56] References Cited

U.S. PATENT DOCUMENTS 5,227,170  7/1993  Sullivan .................................. 424/450

OTHER PUBLICATIONS

Mosser, J., et al., "Putative X–linked Adrenoleukodystrophy Gene Shares Unexpected Homology with ABC Transporters", *Nature*, vol. 361, Feb. 25, 1993, pp. 726–730.
Feil, R., et al., "Adrenoleukodystrophy: A Complex Chromosomal Rearrangement in the Xq28 Red/Green–Color–Pigment Gene Region Indicates Two Possible Gene Localizations", *Am. J. Hum. Genet.*, vol. 49, 1991 pp. 1361–1371.
Aubourg, P., et al., "Frequent Alterations of Visual Pigment Genes in Adrenoleukodystrophy", *Am. J. Hum. Genet*, vol. 42, 1988, pp. 408–413.
Moser, H., et al., "Adrenoleukodystrophy: Phenotypic Variability and Implications for Therapy", *J. Inher. Metab. Dis*, vol. 15, 1992, pp. 645–664.
Valle, D., et al., "Penetrating the Peroxisome", *Nature*, vol. 361, Feb. 25, 1993, pp. 682–683.
Miller et al (1995) FASEB J 9: 190–199.
Culver et al (1994) Trends in Genetics 10: 174–178.
Hodgson (1995) Exp Opin Ther Patents 5: 459–468.
Marshall (1995) Science 269: 1050–1055.
Plummer (1995) Scrip Mag 33: 29–31.
Cartier et al (1996) Arch Pediatr 3(supp 1): 77s–81s.
Shinnoh et al (1995) Biochem Biophys Res Comm 210: 830–836.
Cartier et al (1995) Proc Natl Acad Sci USA 92: 1674–1678.
Orkin et al (1995) Report and Recommendations of the Panel to Assess the NIH Investment in Research on Gene Therapy.
Kaufman (Dec. 4, 1995) Washington Post p. A18.
Martin (1995) Trends in Biotechnology 13: 28–35.
IM Verma et al (1997) Nature 389:239–242.

*Primary Examiner*—Bruce R. Campell
*Attorney, Agent, or Firm*—Young & Thompson

[57] ABSTRACT

A method for the treatment of adrenoleukodystrophy or adrenomyeloneuropathy, in which there is administered to a human patient in need of the same an effective amount of hematopoietic cells modified ex vivo by infection with a retroviral vector containing a nucleic acid fragment comprising a sequence as represented on FIG. 2 (SEQ. ID No: 1) or FIG. 6 (SEQ. ID. No: 4–17) or FIG. 7 (SEQ. ID No: 18–23). Also, human hematopoietic cells can be treated ex vivo to correct the content of very long chain fatty acids in them, by providing human hematopoietic cells of a patient affected by adrenoleukodystrophy or adrenomyeloneuropathy, and infecting them ex vivo with a retroviral vector containing, operably linked to a promoter, a nucleic acid fragment as above. The expression of the nucleic acid in the hematopoietic cells corrects the content of very long chain fatty acids in the hematopoietic cells.

8 Claims, 13 Drawing Sheets

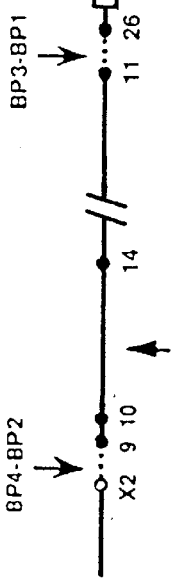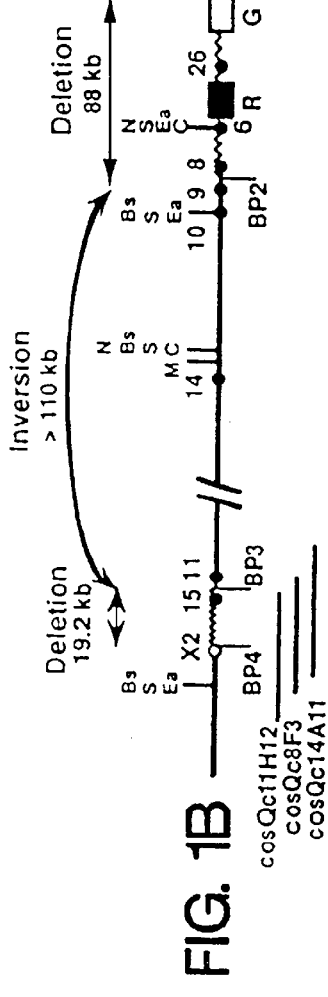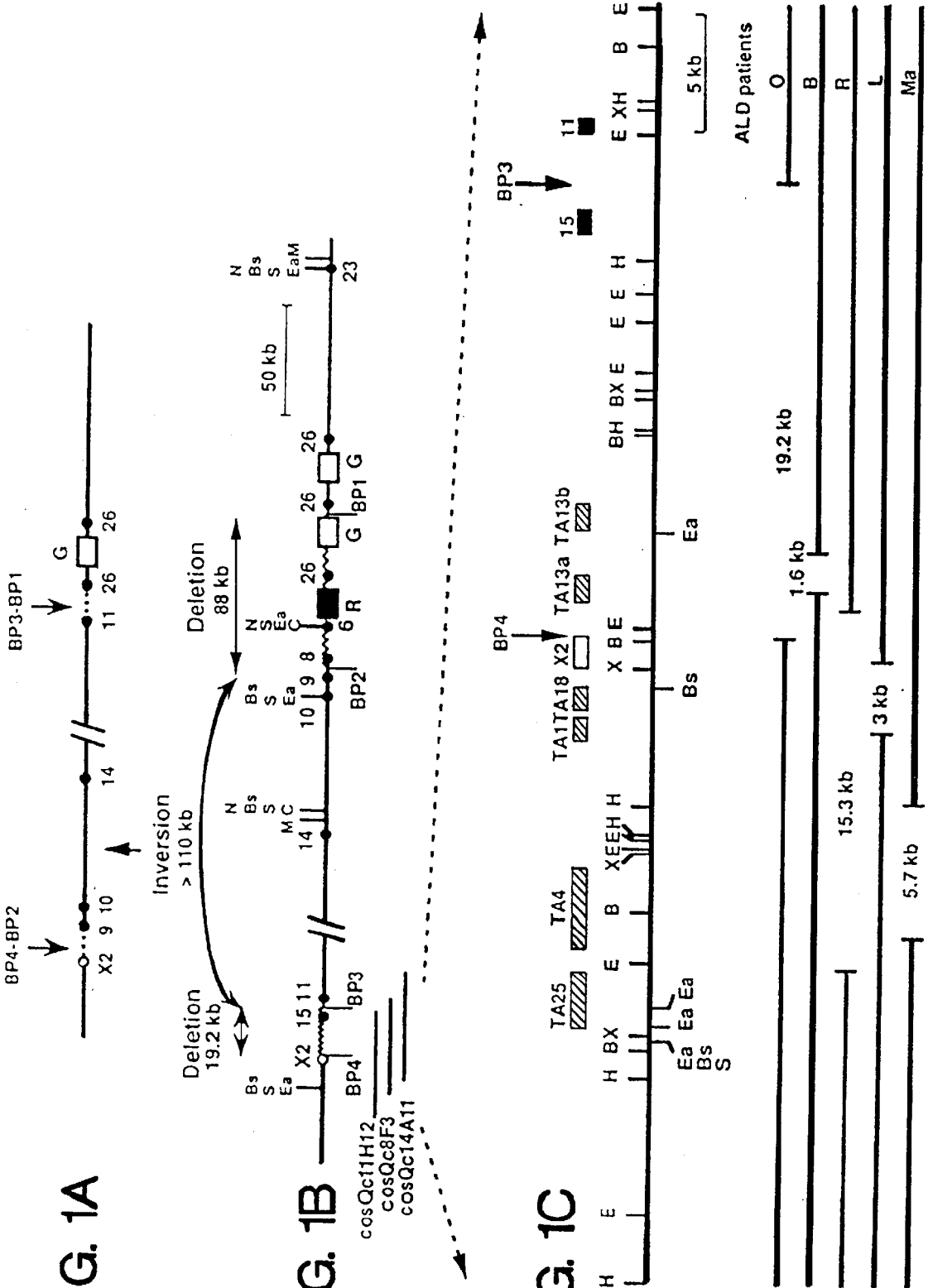
FIG. 1A
FIG. 1B
FIG. 1C

```
PMP70  MAAFSKYLTARNSSLAGAAFLLLCLLHKRRA--LGL--HGKKSGK--PPLQ--NNEKEG       1- 52
       :  :    ::      ::::   ::  :   ::   :     :
ALDP   MPVLSRPRPWRGNTLKRTAVLLALAAYGAHKVYPLVRQCLAPARGLQAPAGEPTQEASGV      1- 60

PMP70  KKERAVVDKVFFSRLIQILKIMVPRTFCKETGYLVLIAVMLVSRTYCDVWMIQNGTLIES     53-112
       :   ::: : :    ::::::  :  :   :::::   ::::: :   ::
ALDP   AAAKAGMNRVFLQRLLWLLRLLFPRVLCRETGLLALHSAALVSRTFLSVYVARLDGRLAR    61-120

PMP70  GIIGRSRKDFKRYLLNFIAAMPLISLVNNFLKYGLNELKLCFRVRLTKYLYEEYLQAFTY    113-172
       :  ::  :  :::: :  : :   ::: ::: ::    :: : :::: ::::
ALDP   CIARKDPRAFGWQLLQWLLIALPATFVNSAIRYLEGQLALSFRSRLVAHAYRLYFSQQTY    121-180

PMP70  YKKGNLDNRIANPDQLLTQDVEKFCNSVVDLYSNLSKPFLDIVLYIFKLTSAIGAQGPA-    173-231
       :   :::::   :       ::  :     :  :  :::          ::
ALDP   YRVSNMDGRLRNPDQSLTEDVVAFAASVAHLYSNLTKPLLDVAVTSYTLLRAARSRGAGT    181-240

PMP70  ---SMMAYLVV--SGLFLTRLRRPIGKMTITEQKYEGEYRYVNSRLITNSEEIAFYNGNK    232-286
          :  :  :    : : : :::   :   ::::::::::::  :::::::::
ALDP   AWPSAIAGLVVFLTANVLRAFSPKFGELVAEEARRKGELRYMHSRVVANSEEIAFYGGHE    241-300

PMP70  REKQTVHSVFRKLVEHLHNFILFRFSMGFIDSIIAKYLATVVGYLVVSRPFL-------    287-338
       :   :::::::  ::: ::  :::  ::::     ::::::
ALDP   VELALLQRSYQDLASQINLILLERLWYVMLEQFLMKYVWSASGLLMVAVPIITATGYSES    301-360

PMP70  --DLSHPRHLKSTHSELL---EDYYQSGRMLLR-MSQALGRIVLAGREMTRLAGFTARIT    339-392
         : :          ::    ::   :  ::: :   : ::  :::    :::  :
ALDP   DAEAVKKAALEKKEEELVSERTEAFTIARNLLTAAADAIERIMSSYKEVTELAGYTARVH    361-420
```

FIG. 4B

```
PMP70  ELMQVLKDLNHGKYERTM-VSQQEK------GIEGVQVIPLIPGAGEIIIADNIIKFDHVP           393-446
       :.::.:  ::.:.:  .: .::.              .:::.                  :
ALDP   EMFQVFEDVQRCHFKRPRELEDAQAGSGTIGRSGVRVEGPLKIRGQVVDVEQGIICENIP           421-480

PMP70  LATPNGDVLIRDLNFEVRSGANVLICGPNGCGKSSLFRVLGELWPLFGGRLTKPERRKLF           447-506
       :.::.:::..::::  :: ::::::::::::::::::: .:: :  ::      :
ALDP   IVTPSGEVVVASLNIRVEEGMHLLITGPNGCGKSSLFRILGGLWPTYGGVLYKPPPQRMF           481-540

PMP70  YVPQRPYMTLGTLRDQVIYPDGREDQKRKGISDLVQKEYLDNVQLGHILEREGGWDSVQD           507-566
       : :::::: .:..::::::: : .:    ::: :::. :.:  :. ..::::: .
ALDP   YIPQRPYMSVGSLRDQVIYPDSVEDMQRKGYSEQDLEAILDVVHLHHILQREGGWEAMCD           541-600

PMP70  WMDVLSGGEKQRMAMARLFYHKPQFAILDECTSAVSVDVEGYIYSHCRKVGITLFTVSHR           567-626
       : :::::::::: .::..:::::: ::::::::: ::::::: :   :   ::. :.::
ALDP   WKDVLSGGEKQRIGMARMFYHRPKYALLDECTSAVSIDVEGKIFQAAKDAGIALLSITHR           601-660

PMP70  KSLWKHHEYYLHMDGRGNYEFKQITEDTVEFGS---------------------------           627-659
       .:::::: :::.:.:: :::::.::.     .:
ALDP   PSLWKYHTHLLQFDGEGGWKFEKLDSAARLSLTEEKQRLECQLAGIPKMQRRLQELCQIL           661-720

PMP70  ------------------------

ALDP   GEAVAPAHVPAPSPQGPGGLQGAST                                              721-745
```

```
                        EXON 1 -              -(1286)- AG
gtggggcaggttggggtgccgggcacggagggaagcgtgtggcagggagg
cccgggggcaggcagccgtgagcggtggggacagtctggggcgggccggg
gctgatgccaaaggtgtgggcaggccatgggagagccgggctggggtggg
--------------------/# 2900 bp/--------------------
cacccaatcgtaacctctggctctcggccttctgatggccaccatggcac
agcgtgtgtgagtggcactgggagaccctgaccatcgccccccacgggagc
tgcccctgtgcatggccaggaagcctctctgtgtctgtcacccccgcag
GT -(1287)-          - EXON 2 -          -(1467)- AG
gtgagacccagggctccaagaggatccaggccaggggcctgtcccccata
ccgctgggtgctgagctcacgagggcccaactcagccagcccgccgccca
cttctgctgccggggccaccgaggccctgctgccagccttgatgctttca
--------------------/# 6600 bp/--------------------
gcacatagagagaaagagagagagagctggttgccccggcaccatttgca
gaagagcctcgcctttctctccagcggctcattttgactttccgctgtc
tctgccctgccccctccccgccccgccacccacccctctggggctttgcag
AT -(1468)-          - EXON 3 -          -(1610)- AG
gtaccctggcccagccccacccttgccatccttgccatgcttctctccc
tgcaactggcaggggctgagccagggtcaccctccctcag
GT -(1611)-          - EXON 4 -          -(1729)- AG
gtaaggctgtcccctccctatgagtgaccccgcccctgctgctgctgcag
gtgctgacctgctgccccagctcctcctattcccgctccctcactcaggg
acctccatgtgcttctggcccatcccagtccacccaggacgggagggctg
--------------------/# 350 bp/---------------------
ctggaccacaggctgctggtcaggaaccagctggcatgctgccagggatg
ggaatgagggcgtgcagccaggggcacgcagactccccagaatgcagagg
ggtcgccaccactccctctccacccagcccgctgtgctgtctctgcag
GC -(1730)-          - EXON 5 -          -(1840)- GG
gtaggtccagcggggagggcgccagccacgcacatatgcaagcctcagcc
cttggcttcccgcctgtctgtgctggcaacagccattgtccctagatgta
cgtggcaggtgggccaaggtcaaggtgagagaccaacgtgtctctgactg
--------------------/# 3000 bp/--------------------
tcccccaggccctgctgtcccttatcaagagatcaagaatggcctgcgtg
ctggcctcgggcattgggagcctctcaaggctggtcaggaggccataggg
tacgcgaagggcctgcgctctctggcgtcagcggctgttgccctgcag
GT -(1841)-          - EXON 6 -          -(1986)- AG
gtaaggaagcccgtgcgcctctcctccacctcttcctgcctgtgcgctca
cacatggcttcctgcagaggcccaggaagtggtgaagagtcagcacctca
ggagaggacactgaggcactgtccccagagccagagacgggctgtggttc
ctgctccctccaaacccgcccgatccactgccctgttttggatctgtgtg
gggtctgtgcacgggcggcgatgtgagcgtgtggatgcgtgtgagcgtgg
catgtggacactgcctggggaggcgcagagtatcttgggggaggcagagcc
ggcccttcctccgtggacacccagctttcccacag
GC -1987)-           - EXON 7 -          -(2132)- AG
gtaggaggcctggggctggcagccacccttgtcccaccctggcctctcc
cttggcctccagggagtgaagattacctcaacatccagagtctaaagtgc
caggtgccacggggcggggcagaggctgctaccagggaggaccaacacca
--------------------/# 1700 bp/--------------------
atgattaatgcctgtcagacagacaaggacgcagaggcacaggggccctg
tcgtcacagctagctcattcccgcagctcccccagctccccggctggccc
ccggctctggtgctggtggaactgagccaagaccattgcccccgcctag
GT -(2133)-          - EXON 8 -          -(2218)- AG
gtgagcactccggaccggcaggctccctggggtccctggaaggggaagt
agcagctgtggggaggcctgggctcagtcgagcctgagccgggctgggt
gttgggccctggagggtgcacagactctcctctcggcccggaccccag
GC -(2219)-          - EXON 9 -          -(2344)- TG
gtaggtgccctgtctccctgcctggggtcggtgggagtgcctgcctgagg
ggaggaggtggcctggcgggccggcagcagcaggcggctgtcatcagca
gcccccgtgccgtgccctgaccctgtccctctcctggccag
GA -(2345)-          - EXON 10

FIG. 6
```

GCGGAGCGGACGACGCGCCTGGTGCCCCGGGAGGGGCGCCACCGGGAGGAGGAGGA
GGAGAAGGTGGAGAGAGGAAGAGACGCCCCTCTGCCCGAGACCTCTCCAAGCCCTGACCTC
AGGGGCCAGGGCACTGACAGGACAGGAGAGCCAAGTTCCTCCACTTGGGCTGCCCGAAGA
GGCCGCGACCCTGGAGGGCCCTGAGCGCCACCGACCCCAGCACCGCACCCACCCCGGGG
GCCTAAAGCGACAGTCTCAGGGGCCATCGCAAGGTTTCCAGTTGCCTAGACAACAGGCCC
AGGGTCAGAGCAACAATCCTTCCAGCCACCTGCCTCAACTGCTGCCCCAGGCACCAGCCC
CAGTCCCTACGCGGCAGCCAGCCAGTGACATGCCGGTGCTCTCCAGGCCCGGCCCTG
GCGGGGAACACGCTGAAGCGCACGCCCGTGCCTCCTGGCCCTCGCGGCCCTATGGAGCCA
CAAAGTCTACCCCTTGGTGCCGCCAGTGCCTGGCCCCGGCCAGGGGTCTTCAGGCGCCGC
CGGGAGCCCACGCAGGAGGCCTCCGGGGTCGCGGCGCGGCCAAAGCTGGCATGAACCGGGT
ATTCCTGCAGCGGCTCCTGTGGCTGCACTCGGCCGCCCTTGGTGAGCGCACCTTCCTGCGGGA
GACGGGGCTGCTGCCGGACGGAAGGCTGGCCTGCCCCTGCCCCAAGGACCCCGGCGGCTTT
TGTGCCCGCCTGCAGCTGCTGCAGCTCGGAGGGCCAACTGGCCTCCTCCTGCTACCTTCGTCAACAGTGC
CATCCGTTACCTGGAGGGCCAACTGGCCTCGTTCCGCAGCCGTCGGTGGCCCACGC
CTACCGCCTCTACTTCTCCCAGCAGACTACTACCGGGTCAGCAACATGGACGGGCGGCT
TCGCAACCCTGACCAGTCTCTGACGGAGGACGTGGTGCCCTTTGCGCCTCTGTGCCCCA
CCTCTACTCCAACCTGAACCAAGCCACTCCTGGACGTGGCTGTGACTTCCTACACCCTGCT
TCGGGCGCCCGCTCCCGTGAGCCGGACAGCCTGGCCTTCTCGCCAAGTTCGGGAGCTGGTGGC
GGTGTTCCTCACGCGCCAACGTGCTGCTGCGGGCTGCGCTACATGCACTCGCGTGTGGTGGCCAACTC
AGAGGAGGCGGCGGAAGGGGGAGCGCTGCGCTACATGCACTCGCGTGTGGTGGCCAACTC
GGAGGAGATCGCCTTCTATGGGGCCATGAGgtgggcaggtgggggcacgga
gggaagcgtgtggcaggaggcccgggggcaggcaggccgtgagccgtggggacagtctgg
ggcgggccgggctgatgccaaagtgtgggcaggccatgggagaggccggggctggggtgg
g

FIG. 7A cacccaatcgtaacctctggctctcggccttctgatggccaccatggcacagcgtgtgtg
agtggcactgggagacccctgaccatcgccccccarggagctgccctgtgcatgccagg
aagcctctctgtgtctgtcaccccccgcagtGGAGCTGGCCCTGCTACAGCGCTCCTAC
CAGGACCTGGCCTCGCAGATCAACCTCATCCTTCTGGAACGCCTGTGTGTATGTTATGCTG
GAGCCAGTTCCTCATGAAGTATGTGGAGCGCCTCCGGCCTGCTCATGGTGGCTGTCCCC
ATCATCACTGCCACTGGCTACTCAGAGTCAGgtgagacccaggyctccaagaggatccag
gccaggggcctgtccccataccgctgggtgctgagctcacgagggccaactcagccag
cccgcgccccacttctgctgccgggggccaccaggccctgctgccagcttgatgctttc
a gcacatagagagagaagagagagagagctggttgccccggcaccatttgcagaagagcctc
gcctttctctccagcggctcattttgactttccgctgtctctgccctgcccctccccgc
cccgccaccacccctctgggctTCTGAGCTTTGCAGATGCAGAGGCCGTGAAGAAGGCAGCCTTGG
AAAGAAGGAGGAGGAGCTGGTGAGCGAGCGCACAGAAGCCTTCACTATGTCCCGCAACC
TCCTGACAGCGGCTGCAGATGCCATTGAGCGGATCATGTCGTCGTACAAGAGGtaccccc
tggcccagccccaccctgccatcctgccatgcttctctccctgcaactggcaggggct
gagccagggtcaccctccctcagTGACGGAGCTGGCTGTCACTTCAAGAGGCCCGGGTGCACG
AGATGTTCCAGGTATTTGAAGATGTTCAGCGCTGCTGTCACTTCAAGAGGCCCAGGAGCTAG
AGGACGCTCAGCGGGGTCTGGGACCATAGCCGTCTGGTGTCCGTGCCCCCTGCTGCTGC
TGAAGATCCGAGtgaaggctgtccctccctatgagtgaccccgcctccctcactcagggacctccat
aggtgctgacctgctgccccagctcctcctattcccgctccctcactcagggacctccat
gtgctttctggcccatcccagtccaccaggacgggagggctg ctggaccacaggctgctggtcaggaaccagctgcatgctgccagggatgggaatgaggg
cgtgcagccaggggcacgcagactcccagaatgcagagggtcgccaccactccctctc
caccccagccccgctgtgctgtcctgcagGCCAGTGGTGGATGTGGAACAGGGGATCA

FIG. 7B

TCTGCGAGAACATCCCCATCGTCACGCCCTCAGGAGAGGTGGTGTGGCCAGCCTCAACA
TCAGGtaggtccagcggggaggggcgccagccacgccacatatgcaagcctcagcccttgg
cttcccgcctgtctgtgctggcaacagccattgtccctagatgtacgtgcaggtgggcc
aagtcaaggtgagagaccaacgtgtctctgactg tcccccaggccctgctgtccctttatcaagagatcaagaatggcctgcgtgctggcctcgg
gcattgggagcctctcaaggctggtcaggaggccataggtacgggaaggggcctgcgct
ctctgcgtcagcggctgttgccctgcagGTGGAGGAAGGCATGCATCTGCTCATCACA
GGCCCAATGGCTGCGCAAGAGCTCCCTGTTCCGGATCCTGGGTGGCTCTGGCCACG
TACGGTGGTGTGCTCTACAAGCCCCCACCCCAGCGCATGTTCTACATCCCGCAGAGtaa
ggaagcccgtgcgcctctcctccaccttcctgctgccgtcacacatggcttcctg
cagagccccaggaagtggtgaagagtcagcacctcaggagagagacactgaggcactgtcc
ccagagcagagacgggctgtgttcctgctccctcccctccaaaccgcccgatccactgccct
gttttggatctgtgtggggtgtgtgcacgggcgatgtgagcgtgtgatgcgtgtga
gcgtggcatgtggacactgcctgggaggcgcagagtatcttgggggaggcagagccggcc
cttccctccgtggacaccagctttcccacagGCCCTACATGTCTGTGGCTCCCTGCGT
GACCAGGTGATCTACCGGACTCAGTGGAGGACATGCAAAGGAAGGGCTACTCGGAGCAG
GACCTGGAAGCCATCCTGGACGTCGTGCACCTGCACCACATCCTGCAGCGGGAGGAGGt
aggaggcctggggctggcagccaccctttgtcccacccctggcctctccctggcctccag
ggagtgaagattacctcaacatccagagtctaaagtgccaggtgccacgggcgggcag
aggctgctaccagggagggaggaccaacacca

FIG. 7C atgattaatgcctgtcagacagacaaggacgcagaggcacagggccctgtcgtcacagc
tagctcattcccgcagctccccagctccccgctgccccggtctgggtgctggtgg
aactgagccaagaccattgcccccgcctagGTTGGGAGGCTATGTGTGACTGGAAGGACG
TCCTGTCGGGTGGCGAGAAGCAGAGAATCGGCATGGCCCGCATGTTCTACCACAGtgag
cactccggaccggcaggctccctgggtccctggaaggggaagtagcagctgtggggag
GCCTGGGCTCAGTGGACCTGAGCCTGGGCTGGGGTGTTGGGCCCTGGAGGGTGCACAGAC
TCTCCTCTCCGGCCCCGGACCCCCAGGCCCAAGTACGCCCTCCTGGATGAATGCACCAGCGC
CGTGAGCATCGACGTGGAAGGCAAGATCTTCCAGGCGGCCAAGGACGCGGGCATTGCCCT
GCTCTCCATCACCACCGGCCCCTCCCTGTGgtaggtgccctgtctccctgcctggggtcg
gtgggagtgcctgcctgcctgaggggaggaggtggcctggcggcccggcagcaggcggct
gtcatcagcagccccgtgccctgaccctgtccctctcctgccagGAAATACC
ACACACTTGCTACAGTTCGATGGGGAGGGCGGCTGGAAGTTCGAGAACAGCTGGACTCAG
CTGCCCGCCTGAGCCTGACGGAGGAGAAGCAGCGGCTGGAGCAGCAGCTGGCGGGCATTC
CCAAGATGCAGCGGCGGCCACCTAGCCCGAAGAGCTCTGCCAGATCCTGGGCGAGCCCTGGCCTCCACCTGAC
CGCATGTGCCGGCCACCTAGCCCGAAGGCCCCCCAAGCTCGGATCACATGAAGGAGACAGCAGC
ACAACCGTCCCCGCCCCTGCCCCCGCCACCCCGCCATGCCTGGCCCCTCCTAGAAAACCCTTC
CCGCC

FIG. 7D

X-LINKED ADRENOLEUKODYSTROPHY GENE AND CORRESPONDING PROTEIN

This application is a division of application Ser. No. 08/136,277, filed Oct. 15, 1993, now U.S. Pat. No. 5,644,045.

The present application relates to the identification and isolation of a gene which is responsible for the adrenoleukodystrophy. It further concerns the protein encoded by this gene and their use in diagnostic or therapeutic procedures.

Adrenoleukodystrophy (ALD) is an X-linked disease affecting 1/20,000 males either as cerebral ALD in childhood or as adrenomyeloneuropathy (AMN) in adults. Childhood ALD is the more severe form, with onset of neurological symptoms between 5–12 years of age. Central nervous system demyelination progresses rapidly and death occurs within a few years. AMN is a milder form of the disease with onset at 15–30 years of age and a more progressive course. Adrenal insufficiency (Addison's disease) may remain the only clinical manifestation of ALD. The principal biochemical abnormality of ALD is the accumulation of very long chain fatty acids (VLCFA) because of impaired β-oxidation in peroxisomes. The normal oxidation of VLCFA-CoA in patients fibroblasts suggested that the gene coding for the VLCFA-CoA synthetase could be a candidate gene for ALD.

ALD or its variant AMN is a monogenic disease but its clinical expression can be under the control of several genes or factors, leading to phenotypic variability.

Adrenoleukodystrophy and adrenomyeloneuropathy are characterized by the presence of an abnormal ALD gene, resulting from deletions or other types of mutations including point mutations. The mutations in the gene may nevertheless remain clinically silent or may lead to various phenotypic clinical expression.

Although it was known that the gene responsible for the adrenoleukodystrophy is located on the Xq28 region of the X chromosome, the results which have been described up to now have not permitted to identify and characterize the gene responsible for the ALD.

Some experiments were for instance conducted in order to check any possible relationship between the alteration of the gene responsible for the colour vision and the ALD gene. The inventors have now shown that although these genes of the red/green colour pigment also map to the Xq28 region, they are not linked either structurally or functionally to the ALD gene.

For the purpose of this description, it is mentioned that the expression "ALD gene" encompasses the gene involved in ALD and also in its adult variant AMN.

The invention accordingly relates to an isolated nucleotide sequence which is for instance selected among DNA, RNA, cDNA sequences, responsible for the adrenoleukodystrophy or the adrenomyeloneuropathy.

By the expression "sequences responsible for ALD or AMN" it must be understood that the abnormal form of the ALD gene is involved in the ALD pathology; of course the normal gene (devoid of mutations, especially of deletions) does not cause the disease.

The term "isolation" refers to the fact that the nucleotide sequence is separated from the other nucleotide sequences of the Xq28 region of the X chromosome when it is purified for instance from a natural source or organism. This isolated nucleotide sequence is also obtainable from synthetic or semi-synthetic sources, according to well-known methods. This sequence can be any type of nucleotide sequence and especially can be selected among DNA, RNA or cDNA.

A particular sequence which is referred to according to the invention consists essentially of the human gene responsible for the ALD. This gene accordingly contains both exons and introns and therefore contains both coding sequences of the gene and regulation sequences.

A preferred embodiment of the invention provides for an isolated nucleotide sequence having the sequence represented on FIG. 6 (SEQ ID Nos.: 4–17) and FIG. 7 (SEQ ID Nos.: 18–23).

The inventors have shown that the gene coding for the ALD protein, contains 10 exons and 9 introns. It must be noted that the deletions and/or mutations which affect the gene and which accordingly are capable of giving rise to the ALD disease or its variant AMN, can be situated either in the exons or in the introns. When these modifications affect the intron sequences, they are often located in the sequence of the intron which is adjacent to the coding sequence. Presence of a mutation in the gene is a condition necessary for the expression of the disease but can remain insufficient to lead to the expression of clinical symptoms related to this disease.

According to another preferred embodiment of the invention, the nucleotide sequence consists of the coding sequence of the gene.

In particular, this coding sequence can be a cDNA corresponding to the sequence represented on FIG. 2 (SEQ ID No.: 1).

According to another embodiment of the invention, the isolated DNA sequence is characterized in that it consists essentially of a DNA sequence encoding the human adrenoleukodystrophy protein. In such a case, the DNA sequence codes for the amino-acid sequence represented on FIG. 2 (SEQ ID No.: 2).

The invention further relates to nucleotide sequences which are modified regarding the above described sequence but which nevertheless hybridize under stringent conditions defined hereafter with a nucleotide sequence as described above. Such a sequence contains preferably at least 10 nucleotides and has advantageously a length of around 20 to 100, preferably 20 to 50 nucleotides.

Figure 5:
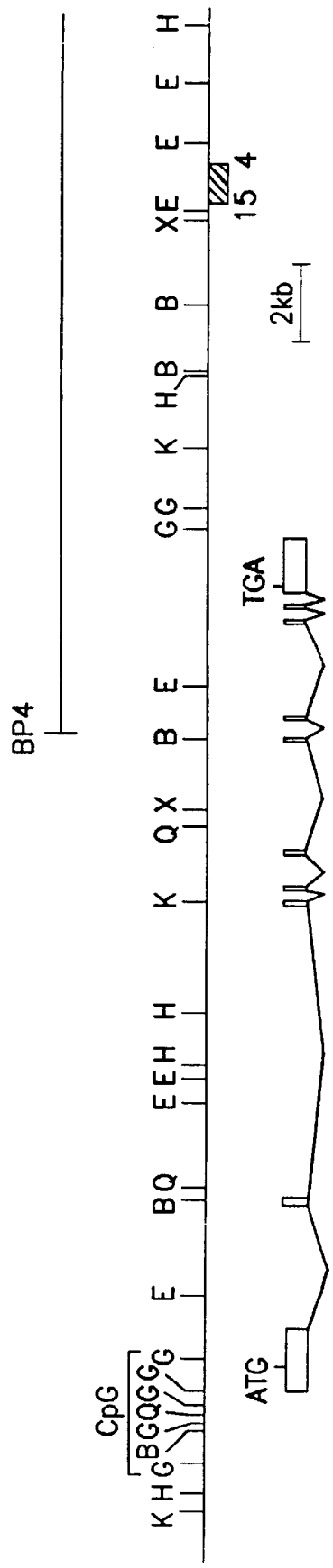

A preferred nucleotide sequence of the invention can further be characterized by the restriction map which is given on FIG. 5 or by the structural organization which is also given on FIG. 5.

The invention also concerns nucleotide fragments selected among DNA or cDNA fragments, which contain at least 10 nucleotides and advantageously at least 20 nucleotides, and are capable of hybridizing specifically, with a sequence which has been defined hereabove.

The hybridization is said specific if the nucleotide fragment does not hybridize for instance with the DNA sequence of the human PMP protein or the DNA of other proteins of the ATP binding protein superfamily.

The fragments of the invention can be labelled in order for instance to be used as probes or can be also involved as primers for amplification reactions and especially for PCR reactions.

The probes of the invention are advantageously labelled by any label classically used. They may be labelled with the aid of a radioactive marker such as $^{32}P$, $^{35}S$, $^{125}I$, $^{3}H$, $^{14}C$ and the radioactive labelling may be performed by any method known to the person skilled in the art.

The probes may be labelled at the 3' end by addition of one or more deoxynucleotides or ribonucleotides or by a dideoxynucleotide labelled in the alpha position by means of $^{32}P$, in the presence of the terminal deoxynucleotidyl transferase, or at the 5' end by transfer of a radioactive phosphate group of a free deoxynucleotide or dideoxynucleotide labelled in the gamma position in the presence of the T4 DNA ligase. The probes may also be labelled by using a DNA polymerase by means of "nick translation" or "random priming" or "polymerase chain reaction".

The method of detection of the hybridization will depend on the radioactive label used and may be based on autoradiography, liquid scintillation, gamma counting or any other technique making possible the detection of the radiation emitted by the radioactive label.

Non-radioactive labelling may also be used by combining with the probes groups exhibiting immunological properties such as an antigen, a specific affinity for certain reagents such as a ligand, physical properties such as fluorescence or luminescence, properties making possible the completion of enzymatic reactions such as an enzyme or an enzyme substrate. The non-radioactive labelling may also be performed directly by chemical modification of the DNA, such as photobiotinylation or sulfonation.

A particular fragment which can be used as a probe is the fragment which is designated by "X2" and which corresponds to an XbaI-EcoRI fragment of 1,8 kb included in the sequence represented on FIG. 6.

Other preferred probes are those designated by Ex13 and Ex3 and represented on FIG. 2.

Particularly preferred fragments to be used as primers for amplification procedures are those which are situated within the sensitive parts of the gene, i.e., the parts which may be more susceptible to mutations or deletions, or also fragments which are surrounding these regions.

Interesting primers are for instance those corresponding to sequences extending from position 1,853 to position 1,872 or from position 1,854 to position 1,874 or from position 2,357 to position 2,375 as shown on FIG. 2 (SEQ ID No.: 1).

The diagnosis can be made to detect the anomaly of the gene in patients presenting clinical symptoms of the disease or unaffected persons capable of transmitting the disease, especially in women carriers or as a neonatal screening.

The invention also concerns a pharmaceutical composition comprising an isolated nucleotide sequence according to the definitions given above, together with a physiological acceptable pharmaceutical vehicle.

A particularly useful pharmaceutical composition is one which contains the genomic DNA of the ALD gene or the cDNA corresponding thereto.

Another aspect of the invention relates to a protein consisting essentially of the adrenoleukodystrophy protein.

In a preferred embodiment, this protein is characterized by the amino-acid sequence given in FIG. 2 (SEQ ID No.: 2).

The invention also relates to a protein having a sufficient homology with the amino-acid sequence given above, to have the essential biological properties of the ALD protein.

These biological properties are the ability to complement the biological defect in cells from patients with ALD or AMN, or to share immunological determinants (epitopes) with the ALD protein.

Another protein within the scope of the invention has the essential biological properties described above and is such that the 52 amino-acid residues of its C-terminal end have an homology of at least 75%, preferably 80% and more preferably 90% with the aligned amino-acid sequence which has been given above.

The invention also relates to amino-acid fragments or sequences containing at least 7 amino-acid residues, which fragments are recognized by antibodies that bind specifically the protein of the invention.

Preferred fragments contain from 7 to around 745 or 500 amino-acids, advantageously from 7 to around 100, preferably from 7 to around 50 and most preferably from 7 to around 20.

Particular amino-acid sequences are derived from regions of the sequence represented on FIG. 2, which are specific for the ALD protein and especially which are not common to sequences of human and rat 70 KPMP protein and other members of the ATP binding protein superfamily, such as those described in the publication of Mosser J. et al (Nature, vol. 361, 25 Feb. 1993, pages 726–730).

The antibodies capable of binding preferably specifically the ALD protein of the invention, especially monoclonal antibodies are obtained according to usual methods, involving the production of hybridoma cells, formed by fusion of spleen cells of an animal previously immunized with a protein of the invention and myeloma cells.

Specific monoclonal antibodies detect a protein having an apparent molecular weight of 75 kDa.

The invention further encompasses the antibodies, either monoclonal or polyclonal that bind specifically the protein according to the above definition.

The specific binding can be checked by assaying these antibodies with proteins having homologies with the ALD protein, for instance with the rat or human 70 peroxisomal membrane protein (PMP) or other proteins of the ATP binding protein superfamily as cited above. The antibodies of the invention are those which do not bind these different proteins presenting some homology with the ALD protein.

The nucleotide sequence or protein or fragments thereof of the invention are useful for diagnostic or therapeutic purposes.

Especially the nucleotide sequences or fragments as defined above can be used in a process for the in vitro diagnosis of the ALD or AMN disease in a human patient, these sequences being used as probes or as primers.

Usual techniques like those which are involved in the detection of genetic diseases are for instance southern blotting RFLP (Restriction Fragment Length Polymorphism) detection or PCR reactions.

The detection of the protein can be performed using specific antibodies, monoclonal or polyclonal.

The detection is performed on samples containing for instance blood cells.

In the present case due to the possibility of various mutations of the ALD gene, it can be useful to have recourse to multiplex PCR, using different primers for amplification of several regions of the gene.

The invention also relates to a process for the treatment of cells and especially somatic cells of a human patient affected by ALD or AMN, comprising the administration to the patient of cells previously modified with a nucleotide sequence as described above. The cells can be modified by recombinant nucleotide sequences containing one of the DNA, cDNA or RNA sequence of the invention, under the control of regulation elements in a vector appropriate for the modification or transfection of cells. Advantageously the regulation elements are capable of ensuring a high level of expression and comprise accordingly strong promoters, possibly an enhancer and in some instances a reporter gene such as for example the neo gene or the dhfr gene.

Appropriate vectors can be plasmid vectors, retroviruses vectors or for instance adenoviruses vectors.

The transfer of the sequence useful for therapeutic purposes is performed by ex vivo techniques like electroporation, transfection especially calcium phosphase transfection or fusion for instance with liposomes.

The somatic transfer can also be performed in vivo using cells as vectors, which cells are previously modified ex vivo with the gene of interest. Accordingly hematopoietic cells or nervous cells are used. Among the techniques which are available for in vivo transfer of gene one can further cite inert vectors like liposomes, viral vectors, especially retroviruses or adenoviruses or directly by injection of DNA.

The vectors used for the somatic transfer of the gene or sequences of the invention can also be directly transferred in vivo, for instance by direct injection in the blood stream or by stereotactic injection in specific regions of the brain (Strattford-Perricaudet L D et al J Clin Invest 90,626–630. Akli S et al Nature genomics vol 3, March 1993).

The direct administration of DNA has been described for instance by Wolff J. A. et al (1990, Science 247, 1465–1468) or Acsadi G. et al (1991, Nature 352, 815–818).

As example, for the preparation of the vector, the sequence of the ALD gene, preferably the cDNA corresponding to the ALD gene is inserted in a defective murine Moloney vector (Mo-MLV), under the control of regulation elements. The defective vector still contains its cis-sequences such as the LTR sequence or part thereof sufficient for the transcription and integration, the psi sequence necessary for the encapsidation and the PB sequence for viral replication. In this vector the viral genes gag, pol, env are at least partly deleted and substituted with the sequence of interest. This sequence is placed under the control of its own promoter or a stronger promoter such as the SV40 promoter. A marker gene is possibly added to the construction.

The helper virus used contains the retroviral genes (gag, pol, env) necessary for replication of the viral genome and for the formation of the viral particles. To the contrary the cis-sequences which are present in the vector are deleted in the helper virus.

The helper provirus is inserted in a murine cell line especially NIH/3T3 as host.

The vector is then transfected in the cell line allowing the production of viral particles.

From a general point of view, the techniques used for the transfer of the human ADA gene (Adenosine desaminase) in cells can be also used in the present situation. Like the ADA gene, the ALD gene or its cDNA is transfected with a retrovirus in fibroblast cells (Palmer et al. PNAS, 1987, 84, 1055–1059), or in lymphocytes or other hematopoietic cells including precursor or stem cells (Culver et al. Hum Gene Ther 2,107 1991 or Anderson W F Science vol 256 May 6 1992, p808)

Other characteristics and advantages of the invention will become apparent from the examples and figures.

FIGURES

FIGS. 1A–1E Map of the ALD gene region and its rearrangements in patients. a, Chromosomal rearrangement in patient O. The joining of BP4-BP2 and BP3-BP1 were demonstrated by cloning the corresponding junction fragments (dashed lines). The extends of the two deletions (19.2 and 88 kb respectively) are indicated in b. Probe X2 (circle) is discussed in the examples and other probes (filled circles, Fr probes) are from Martinez, C. M. et al, (Cell Biol. int. Rep. 14, 255–266, 1990). The distance between probes Fr14 and Fr11 (broken line) is not known. The green cone pigment gene (GCP) is indicated by a box (G). b, Map of the R/GCP genes and of the second deletion in patient O, including the rare cutter restriction sites (vertical bars, top) EagI (Ea), BssHII (Bs), SacII (S), ClaI (C), NotI (N) and MluI (M). The rare cutter sites within the pigment gene repeat unit are not marked. The extents of the two deletions (wavy lines) and the position of the 4 BPs in patient O are indicated. Probe Fr15.4 (deleted in patient O) was used to screen a Xq28-specific cosmid library, yielding 3 overlapping clones (cos Qc 11H12, cos Qc 8F3 and cos Qc 14A11). The red cone pigment (RCP) gene is indicated by the filed box (R) and the GCP gene by a box (G. c, Deletions detected in 5 ALD patients and restriction map of the subcloned region of ALD gene using the following enzymes: EcoRI (E), HindIII (H), BamHI (B), and XbaI (X). Rare cutter sites are indicated as in b. Localization of subcloned probes is shown at the top. Probe X2 (box) is a 1.8 kb XbaI-EcoRI restriction fragment derived from X-8, the second junction fragment (BP4-BP2) in patient O. TA25 (2.1 kb), Ta4 (3.6 kb), Ta1 (1.0 kb), Ta18 (0.85 kb), Ta13a (935 bp) and Ta13b (252 bp) are TaqI-digested DNA fragments (hatched boxes) derived from subcloning of cosmid Qc 11H12. d, Segregation of an abnormal junction fragment detected by probe X2 in ALD family B. Probe X2 hybridizes to a 16-kb HindIII fragment in normal individuals (open square and circle). An abnormal 14.4-kb junction fragment was detected in an affected ALD patient (patient B; see panel c) and in all heterozygous females (). e, Detection of the same rearranged DNA fragment in two ALD brothers with different clinical ALD phenotypes by Southern blot analysis of HindIII-digested DNA from 3 brothers (Family Ma; see c) hybridized with probe X2. An abnormal junction fragment of 22 kb is detected by X2 in a male with cerebral ALD (filled square) and his brother with Addison's disease (hatched square).

METHODS. Restriction patterns of the cosmids were analyzed as described. Cosmid Qc 11H12 was digested with TaqI and cloned directly in the ClaI site of pBluescript SK$^+$ (Stratagene). X-8 was isolated from a XbaI genomic library constructed in bacteriophage X (Stratagene) using DNA from a somatic hybrid line containing the X chromosome of patient O. Gel electrophoresis, Southern blotting, probing and autoradiography were all done as described.

Figure 2B:
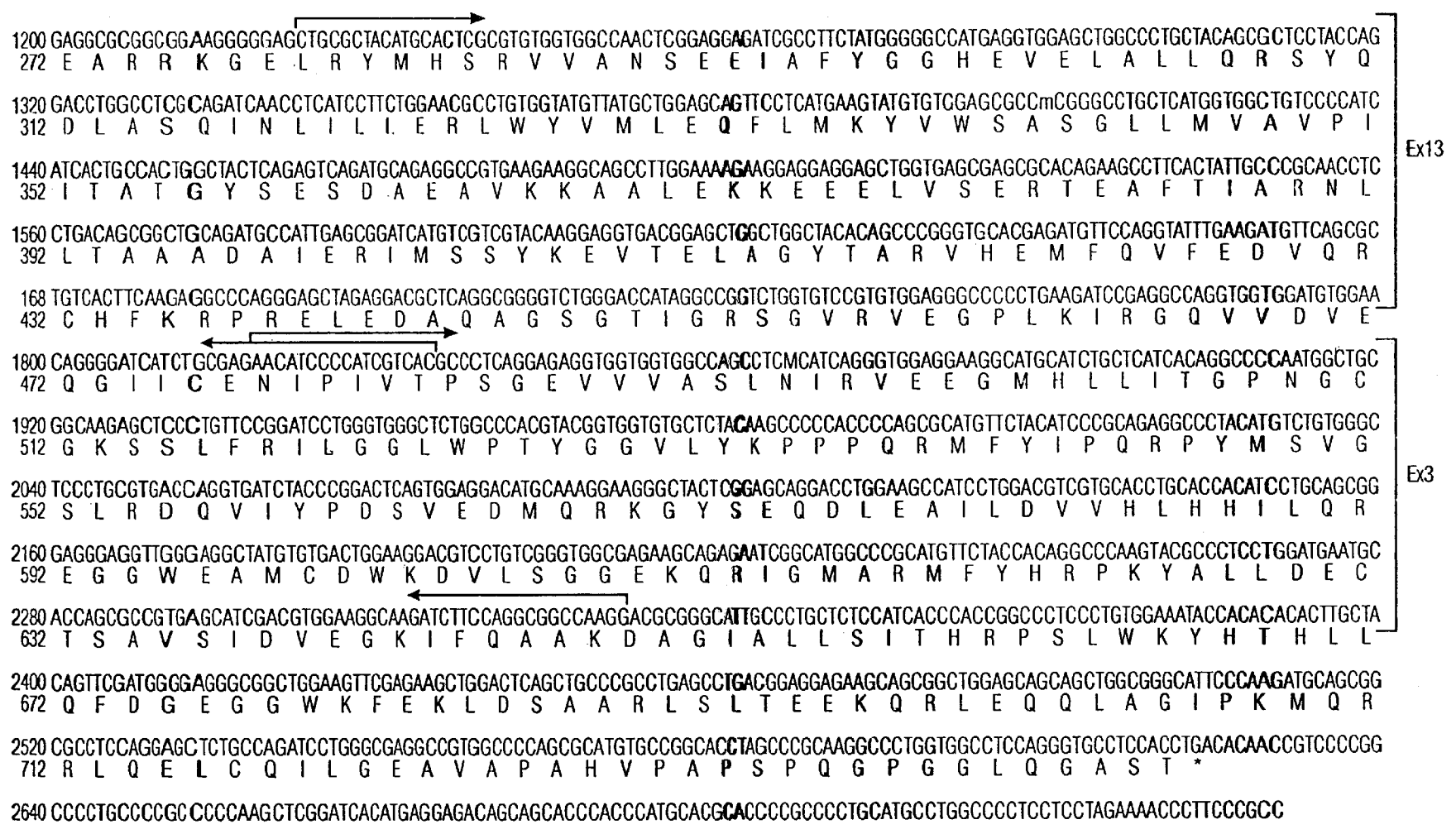

FIGS. 2A–2B. Sequence of ALD-protein cDNA (SEQ ID Nos: 1 and 2). The sequence is derived from analysis of clones obtained by exon connection and clones isolated from a HeLa cDNA library, and confirmed in most cases by sequences of genomic clones.

METHODS. Four probes (Ta25, Ta1, Ta18 and TA13b) derived from subcloning of cosmid Qc 11H12 were sequenced. Candidate exons, strand and frame assignments were screened by the GRAIL program (Oak Ridge, RN). Oligonucleotide primers were designed according to the coding regions that presented highest homology score to 70K PMP in TA25, TA18, and TA13b. Ex13 and Ex3 are cDNA clones obtained by exon connection in 2-step-boosted or nested polymerase reactions (30 cycles with external primers and 40 cycles with internal primers) performed on oligo(dT)-primed cDNA Total RNA (20 $\mu$g) from a lymphoblastoid cell line was used as starting material. External primers correspond to positions 1,853–1,872 (for Ex13), and to positions 1,854–1,874 and 2,357–2,375 (for Ex3). Internal primers are indicated by arrows. Subsequent amplification products were blunt-ended by action of T4 DNA polymerase (New England Biolabs), directly cloned in pBluescript KS$^+$ vector (Stratagene), sequenced using dideoxynucleotide termination (applied Biosystems), and analyzed on an automated DNA sequencer (Applied Biosystems).

Figures 3A, 3B:
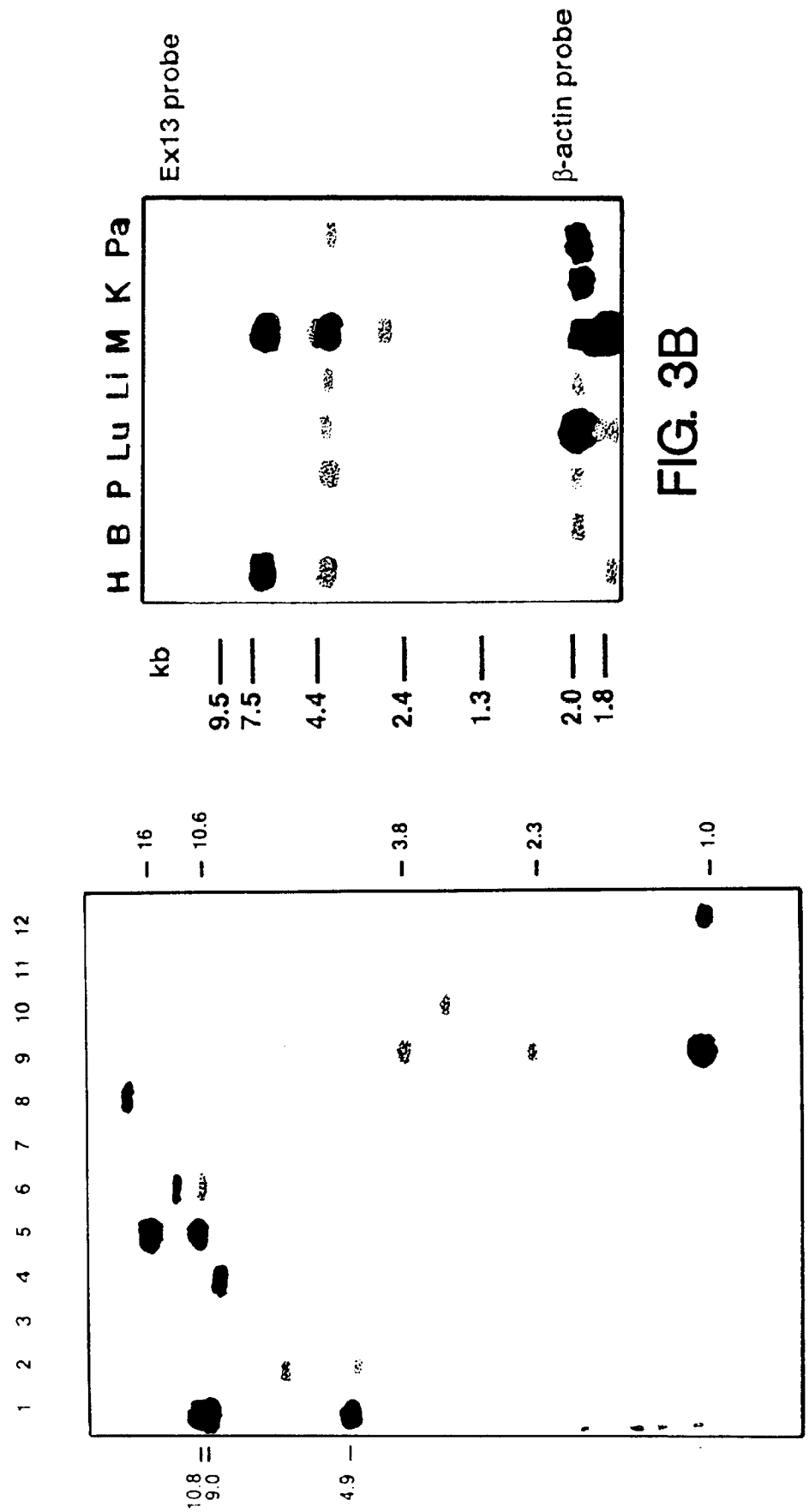

FIGS. 3a–3b, Detection of deletions in the DNA isolated from three ALD patients using cDNA probe Ex13. DNA was digested with EcoRI (lanes 1–4), HindIII (lanes 5–8) and TaqI (lanes 9–12). Lanes 1, 5 and 9: normal woman; lanes 2, 6 and 10: patient L; lanes 3, 7 and 11: patient R; lanes 4, 8 and 12: patient Ma. The 10.8-kb EcoRI normal fragment (lanes 2–4) and the 12.5-kb HindIII abnormal junction fragment from patient R (lane 7) hybridize to only around 60 bp of the Ex13 probe and are thus very fait. Sizes (in kb) of normal restriction fragments are indicated on the left and on the right. Similar results were obtained with Ex3 in ALD patients deleted in 3' end region of the ALD gene. b, Northern blot analysis with probe ex13. cDNA Ex13 hybridized to northern blot (top) of human poly(A)$^+$ RNA detects a transcript of 4.2 kb which is expressed in heart (H), placenta (P), lung (Lu), liver (Li) skeletal muscle (M), pancreas (Pa) and, to a lesser extent, in brain(B) and kidney (K). Two other transcripts are detected in heart and skeletal muscle (6.8 kb) and in liver and skeletal muscle (2.75 kb). RNA size markers are indicated on the left. A human β-actin probe hybridized to the same northern blot (bottom panel) detects two transcripts of 2.0 and 1.8 kb, respectively.

METHODS. Gel electrophoresis, Southern blotting, probing and autoradiography were done as described. For b, human multiple-tissue northern blot was purchased from Clontech. Membranes were exposed at –70° C. to X-ray film for 5d (Ex13 or EX3 probes) or for 6 h (β-actin probe).

FIGS. 4A–4B. Sequence alignment of ALD protein (SEQ ID No.: 2) and human 70 K PMP (SEQ ID No.: 3). Amino acid identities are indicated by two dots and conservative changes by one. Sequence similarities were established with the FASTP program.

FIG. 5. Structural organization of the ALD gene (SEQ ID Nos.: 4–17) The distribution of the 10 ALD exons is shown with black boxes. Traduction initiation and termination sites (respectively in exon 1 and 10) are indicated. The location of the CpG island, the genomic probe FR15.4 (grey box) and the most centrometric breakpoint of patient O rearrangement (BP4) are also represented.

FIG. 6. Intron-exon boundaries of the ALD gene (SEQ ID Nos.: 18–23). First and last two bases of each exon are indicated in bold. The position (number between brackets) correspond to the published cDNA sequence (Mosser et al, Nature). The average size of the gap within the sequence is specified for large introns. Sequence of small introns is fully represented.

FIGS. 7A–7D. Complete DNA sequence of the ALD gene. It contains both the cDNA sequence (in capital letters) and the intron sequence (in small letters).

EXAMPLES

I) Isolation and identification of the ALD gene

Here a positional cloning was used to identify a gene partially deleted in 6 of 85 independent patients with ALD. In familial cases, the deletions segregated with the disease. An identical deletion was detected in two brothers presenting with different clinical ALD phenotypes. Candidate exons were identified by computer analysis of genomic sequences and used to isolate complementary DNAs by exon connection and screening of cDNA libraries. The deduced protein sequence shows significant sequence identity to a peroxisomal membrane protein of $M_r$ 70K that is involved in peroxisome biogenesis and belongs to the "ATP-binding cassette" superfamily of transporters.

As previous attempts to purify VLCF-CoA synthetase were unsuccessful, a "positional cloning" approach was used. The ALD locus has been mapped to Xq28 (deDuve, C. et al, Biochem. Pharmac. 23, 2495–2531, 1974), where the red/green colour pigment (R/GCP) genes reside. On the basis of the high incidence (40%) of colour vision anomalies in AMN patients and earlier results, it was firstly proposed that ALD and R/GCP genes could be close together. Recently, an AMN patient with blue-monochromatic colour vision was identified who had a complex rearrangement located 5' of the red-colour pigment (RCP) gene, which included two deletions separated by a large (>110 kb) inversion (FIG. 1a and b). Only the RCP gene was found in the first deletion (88 kb). No additional deletion was detected in this region in 81 other ALD patients. It was then postulated that the inverted segment or the second deletion were candidate loci for the ALD gene.

Probes corresponding to three of the breakpoints (BP) of this rearrangement were isolated (BP1, BP2 and BP3) (FIG. 1). To estimate the size of the second deletion, a probe 4 kb proximal to Fr15 was used (deleted in patient O; Martinez et al, Cell Biol. Int. Rep. 14, 255–266 (1990) to obtain clones from a Xq28 cosmid library. Three overlapping clones were obtained that spanned about 90 kb and contained a cluster of rare restriction cutting sites (EagI, BssHII, SacII) indicating the presence of a CpG island (FIG. 1c). In parallel, an XbaI junction fragment (X-8) corresponding to breakpoints 4 and 2 in patient O was cloned (FIG. 1a). A restriction map of X-8 showed that a 1.8 kb XbaI-EcoRI (X2) fragment contains a 1.6-kb segment on the BP4 side and included within the Fr15 cosmid contig described above (FIG. 1b and c). Breakpoints 3 and 4 are separated by 19.2 kb, and delimit the second deletion in patient O.

Figure 1D:
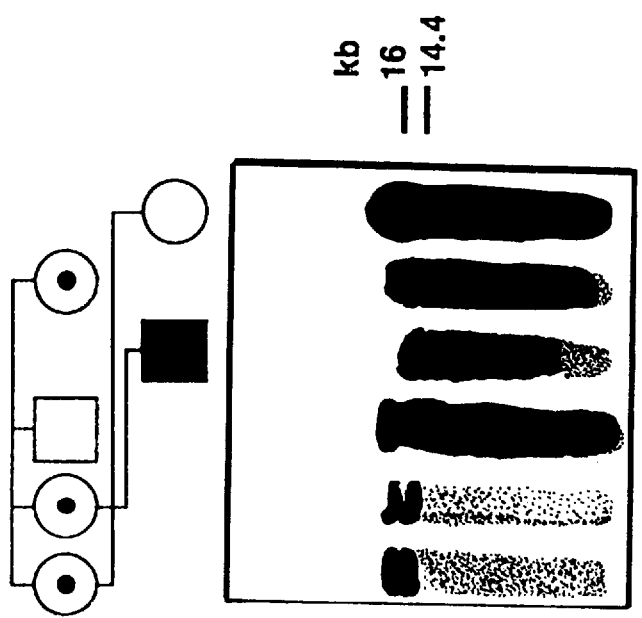

To search for conserved sequences in other mammalian species and to detect additional deletions in other ALD patients, cosmid Qc 11H12 was subcloned (FIGS. 1b, c). Probes TA25, TA1, TA18 and TA13B (FIG. 1c) showed cross-hybridization to various mammalian species. More important, X2, TA4, TA18 and Ta13a probes detected deletions in five other ALD patients. Probe X2 allowed the detection of a junction fragment segregating with the disease in family B (FIG. 1d). In another family (Ma), probe X2 detected an identical 22-kb HindIII junction fragment in two brothers with different clinical phenotypes of ALD (FIG. 1e). The size of deletions ranged from 1.6 kb (patient B) to 15.3 kb (patient R) with partial overlap (FIG. 1c). Six patients had deletions (including patient O) in a population of 85 independent ALD patients, but no deletions were found in a panel of 82 control males. These results indicate that the region contains at least part of the ALD gene.

The sequences of probes Ta25, TA18, TA13b and of TA13a were determined and examined for putative coding regions (using a computer program based on a multiple sensor-neural network approach) revealed a large (>700bp) putative protein coding sequence within TA25 and smaller open reading frames (300–400 bp) in TA18, TA13a and TA13b. The deduced amino-acid sequences showed significant sequence identity with collinearly positioned regions of human or rat 70K peroxisomal membrane protein (PMP). Nested-PCR reactions using primers from the putative exons (FIG. 2) (SEQ ID No.: 1) produced two fragments (Ex13 and Ex3) of sizes (645 bp and 498 bp, respectively) compatible with those expected from homology with the 70K PMP cDNA (SEQ ID No.: 3). They hybridized to the predicted DNA fragments in normal individuals and to the same fragments detected by genomic probes in ALD patients (FIG. 3a). Ex13 and Ex3 have been used in combination to screen a random-primed HeLa cell cDNA library to obtain 6 independent overlapping clones.

The 2,751-bp sequence (FIG. 2) contains the whole protein-coding sequence of 745 amino acids (SEQ ID No.: 2). The first methionine codon is preceded by an in-phase stop codon (at bp 282) and is included within a potential ribosome-binding sequence. Significant sequence identity with the 70K PMP (SEQ ID No.: 3) begins at methionine 67 and ends at around 680 (corresponding to the carboxy terminus of 70K PMP). The remaining 52 amino acid residues are unique to the ALD protein (SEQ ID No.: 2) (FIG. 4a).

The sequence of ALD protein could be aligned with human 70K PMP (SEQ ID No.: 3) (Saari, J. C. & Bredberg, L. Biochim. biophys. Acta 716, 266–272, 1982)) with only a few deletions or insertions, and revealed a 38.5% amino-acid identity (253/659 amino acids) (FIG. 4a). When conservative amino acids substitutions are considered, the sequence similarity between the two protein sequences reached 78.9%. The two proteins show a similar hydrophobicity profiles, with a hydrophobic amino-terminal region containing potential transmembrane segments.

The hydrophilic carboxy-terminal region of the ALD protein shows 56% identity over 210 amino acids to the corresponding region of 70K PMP. The two characteristic nucleotide-binding consensus sequences are almost identical between the two proteins (underlined in FIG. 4b).

When northern blots of poly(A)$^+$ RNAs from human tissues were hybridized to probes Ex13 or Ex3, a transcript of 4,2 kb was detected in heart, placenta, lung, liver, skeletal muscle, testis, pancreas and, to a lesser extent, in brain and kidney (FIG. 3b). The expression of the 4.2-kb transcript was very low in adult brain but more marked in 21-week fetal brain. A second transcript of 6.8 kb was detected in heart and skeletal muscle, whereas a third transcript of 2.75 kb was detected in muscle and liver. These additional transcripts could arise from alternative processing or the use of multiple polyadenylation sites. The sequence shown in FIG. 2 corresponds to 4.2-kb messenger RNA, this being the only species detected in HeLa cells.

The putative ALD gene has thus been identified in the distal part of Xq28 which has deletions in one or several exons in 6 of 85 independent ALD patients. Some of these deletions are small and non-overlapping, thus strengthening the conclusion that this gene is indeed involved in ALD. Although the gene coding for VLCFA-CoA synthetase was considered as a candidate gene for ALD, a recently cloned rat gene for long-chain ($C_{12}$–$C_{16}$)acyl-CoA synthetase failed to detect homologous sequences on the X chromosome. The putative ALD gene shows no homology to this latter sequence, or to the three other enzymes involved in peroxisomal β-oxidation. Surprisingly, a very significant sequence identity was found with human and rat 70K PMP. Two putative domains could be identified by hydropathy analysis: an amino-terminal hydrophobic region, which presumably contains six transmembrane segments, and a hydrophilic region containing ATP-binding motifs with striking identity to the ATP-binding region of the human 70K PMP. This sequence is well conserved in the ATP-binding cassette (ABC) family of transporters, which includes the multidrug-resistant gene product, the cystic fibrosis transmembrane conductance regulator, and the products of the PSF1 and PSF2 genes, which encode peptide transporters and map in the class II region of the human MHC complex (FIG. 4b). The conserved region includes the A and B consensus sequences (A; G-X4-G-K-T-X6-I/V; B: R/K-X3-G-X3-L (hydrophobic)4-D) of a nucleotide-binding fold, plus a 12-amino-acid motif highly conserved in ABC proteins (FIG. 4b).

ALD protein must therefore be a member of this superfamily of ABC transporters, which are also involved in transport of proteins, amino acids, inorganic ions and peptides in prokaryotes and eukaryotes. Although the predicted sequence of ALD protein (SEQ ID No.: 2) shows significant identity to 70K PMP (SEQ ID No.: 3), no homology was found to 35K PMP or to other PMPs required for peroxisome biogenesis in yeast. Although ALD was initially thought to involve a deficiency in peroxisomal VLCFA-CoA synthesase, the predicted sequence of the putative ALD protein rather suggests a protein involved in transport of VLCFA-CoA synthetase into the peroxisomal membrane or a protein that is functionally associated with the VLCFA-CoA synthetase in the peroxisomal membrane. The translocation of acyl-CoA oxidase, the next enzyme or the peroxisomal β-oxidation pathway, requires ATP hydrolysis, whereas the transport of VLCFA across the peroxisomal membrane does not, and neither is it impaired in peroxisomes from ALD patients.

Expression of ALD protein was observed in every tissue tested, but the relationship between ALD protein expression and the abundance of peroxisomes in tissues may not be straight-forward. Perosisomes are particularly abundant in liver and kidney, having an average diameter of 0.2–1 $\mu$M. In other tissues, including the brain and fibroblasts, they are less abundant and smaller (0.05–0.2 $\mu$M). This abundance and size difference may reflect a distinct membrane and matrix protein compositions of peroxisomes in different tissues. Although ALD is associated with a defective oxidation of VLCFA, this metabolic defect is mainly expressed in brain and adrenal tissues.

ALD is characterized by a striking variation in clinical phenotype. In family Ma, an identical deletion was found in two sibs, a boy who developed cerebral ALD at 8 years, and his brother who developed only very mild adrenal insufficiency at 13 years. Furthermore, deletions were associated with the adult form (patients O and R) as well as with the severe childhood form (patients B and L). These differences suggest that the phenotypic variability of ALD is probably due to secondary factors (possibly immunological) or to the influence of still unidentified modifier genes.

II) Transfer and expression of the cDNA sequence of the ALD gene 1) retroviral vector A defective murine Moloney vector (Mo-MLV) is used.

The defective vector still contains its cis-sequences such as the LTR sequence or part thereof sufficient for the transcription and integration, the psi sequence necessary for the encapsidation and the PB sequence for viral replication. In this vector the viral genes gag, pol, env are at least partly deleted.

The promoter of the ALD gene or advantageously a stronger promoter such as the PGK-1 promoter (phosphoglycerate kinase) or SV40 promoter replaces the deleted viral genes.

The cDNA of the ALD gene is cloned within the defective vector, under the control of the promoter, in a chosen restriction site.

The retroviral vector is then introduced in a cell line for encapsidation, which cell line expresses the gag, pol and env viral genes. A cell line like NIH/3T3 previously modified with the helper virus (Danos et al, PNAS, 85, 6460–6465, 1988) is used.

The recombinant construct is introduced by transfection and the cells produce viral particles.

2) Infection of cells

The cells used for the transfer of the cDNA sequence are cultivated and contacted and incubated with the retroviral vector. The infected cells are then amplified sufficiently to be used for the treatment.

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 2750 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 387..2624

( x i ) SEQUENCE DESCRIPTION: SEQ ID NO:1:

```
GCGGACGGAC   GCGCCTGGTG   CCCCGGGGAG   GGGCGCCACC   GGGGGAGGAG   GAGGAGGAGA                        60

AGGTGGAGAG   GAAGAGACGC   CCCCTCTGCC   CGAGACCTCT   CAAGGCCCTG   ACCTCAGGGG                       120

CCAGGGCACT   GACAGGACAG   GAGAGCCAAG   TTCCTCCACT   TGGGCTGCCC   GAAGAGGCCG                       180

CGACCCTGGA   GGGCCCTGAG   CCCACCGCAC   CAGGGGCCCC   AGCACCACCC   CGGGGGCCTA                       240

AAGCGACAGT   CTCAGGGGCC   ATCGCAAGGT   TTCCAGTTGC   CTAGACAACA   GGCCCAGGGT                       300

CAGAGCAACA   ATCCTTCCAG   CCACCTGCCT   CAACTGCTGC   CCCAGGCACC   AGCCCCAGTC                       360

CCTACGCGGC   AGCCAGCCCA   GGTGAC ATG CCG GTG CTC TCC AGG CCC CGG CCC                             413
                               Met Pro Val Leu Ser Arg Pro Arg Pro
                                 1               5

TGG CGG GGG AAC ACG CTG AAG CGC ACG GCC GTG CTC CTG GCC CTC GCG                                  461
Trp Arg Gly Asn Thr Leu Lys Arg Thr Ala Val Leu Leu Ala Leu Ala
 10              15                  20                      25

GCC TAT GGA GCC CAC AAA GTC TAC CCC TTG GTG CGC CAG TGC CTG GCC                                  509
Ala Tyr Gly Ala His Lys Val Tyr Pro Leu Val Arg Gln Cys Leu Ala
                     30              35                  40

CCG GCC AGG GGT CTT CAG GCG CCC GCC GGG GAG CCC ACG CAG GAG GCC                                  557
Pro Ala Arg Gly Leu Gln Ala Pro Ala Gly Glu Pro Thr Gln Glu Ala
             45                  50                  55

TCC GGG GTC GCG GCG GCC AAA GCT GGC ATG AAC CGG GTA TTC CTG CAG                                  605
Ser Gly Val Ala Ala Ala Lys Ala Gly Met Asn Arg Val Phe Leu Gln
                 60              65                      70

CGG CTC CTG TGG CTC CTG CGG CTG CTG TTC CCC CGG GTC CTG TGC CGG                                  653
Arg Leu Leu Trp Leu Leu Arg Leu Leu Phe Pro Arg Val Leu Cys Arg
     75                      80                  85

GAG ACG GGG CTG CTG GCC CTG CAC TCG GCC GCC TTG GTG AGC CGC ACC                                  701
Glu Thr Gly Leu Leu Ala Leu His Ser Ala Ala Leu Val Ser Arg Thr
 90              95                  100                     105

TTC CTG TCG GTG TAT GTG GCC CGC CTG GAC GGA AGG CTG GCC CGC TGC                                  749
Phe Leu Ser Val Tyr Val Ala Arg Leu Asp Gly Arg Leu Ala Arg Cys
                     110             115                     120

ATC GCC CGC AAG GAC CCG CGG GCT TTT GGC TGG CAG CTG CTG CAG TGG                                  797
Ile Ala Arg Lys Asp Pro Arg Ala Phe Gly Trp Gln Leu Leu Gln Trp
             125                 130                 135

CTC CTC ATC GCC CTC CCT GCT ACC TTC GTC AAC AGT GCC ATC CGT TAC                                  845
Leu Leu Ile Ala Leu Pro Ala Thr Phe Val Asn Ser Ala Ile Arg Tyr
             140                 145                 150

CTG GAG GGC CAA CTG GCC CTG TCG TTC CGC AGC CGT CTG GTG GCC CAC                                  893
Leu Glu Gly Gln Leu Ala Leu Ser Phe Arg Ser Arg Leu Val Ala His
     155                     160                 165
```

```
GCC  TAC  CGC  CTC  TAC  TTC  TCC  CAG  CAG  ACC  TAC  TAC  CGG  GTC  AGC  AAC       941
Ala  Tyr  Arg  Leu  Tyr  Phe  Ser  Gln  Gln  Thr  Tyr  Tyr  Arg  Val  Ser  Asn
170            173       175                 180                           185

ATG  GAC  GGG  CGG  CTT  CGC  AAC  CCT  GAC  CAG  TCT  CTG  ACG  GAG  GAC  GTG       989
Met  Asp  Gly  Arg  Leu  Arg  Asn  Pro  Asp  Gln  Ser  Leu  Thr  Glu  Asp  Val
                    190                 195                      200

GTG  GCC  TTT  GCG  GCC  TCT  GTG  GCC  CAC  CTC  TAC  TCC  AAC  CTG  ACC  AAG      1037
Val  Ala  Phe  Ala  Ala  Ser  Val  Ala  His  Leu  Tyr  Ser  Asn  Leu  Thr  Lys
                    205                 210                      215

CCA  CTC  CTG  GAC  GTG  GCT  GTG  ACT  TCC  TAC  ACC  CTG  CTT  CGG  GCG  GCC      1085
Pro  Leu  Leu  Asp  Val  Ala  Val  Thr  Ser  Tyr  Thr  Leu  Leu  Arg  Ala  Ala
          220                      225                           230

CGC  TCC  CGT  GGA  GCC  GGC  ACA  GCC  TGG  CCC  TCG  GCC  ATC  GCC  GGC  CTC      1133
Arg  Ser  Arg  Gly  Ala  Gly  Thr  Ala  Trp  Pro  Ser  Ala  Ile  Ala  Gly  Leu
     235                      240                      245

GTG  GTG  TTC  CTC  ACG  GCC  AAC  GTG  CTG  CGG  GCC  TTC  TCG  CCC  AAG  TTC      1181
Val  Val  Phe  Leu  Thr  Ala  Asn  Val  Leu  Arg  Ala  Phe  Ser  Pro  Lys  Phe
250                      255                      260                      265

GGG  GAG  CTG  GTG  GCA  GAG  GAG  GCG  CGG  CGG  AAG  GGG  GAG  CTG  CGC  TAC      1229
Gly  Glu  Leu  Val  Ala  Glu  Glu  Ala  Arg  Arg  Lys  Gly  Glu  Leu  Arg  Tyr
                    270                      275                           280

ATG  CAC  TCG  CGT  GTG  GTG  GCC  AAC  TCG  GAG  GAG  ATC  GCC  TTC  TAT  GGG      1277
Met  His  Ser  Arg  Val  Val  Ala  Asn  Ser  Glu  Glu  Ile  Ala  Phe  Tyr  Gly
               285                      290                      295

GGC  CAT  GAG  GTG  GAG  CTG  GCC  CTG  CTA  CAG  CGC  TCC  TAC  CAG  GAC  CTG      1325
Gly  His  Glu  Val  Glu  Leu  Ala  Leu  Leu  Gln  Arg  Ser  Tyr  Gln  Asp  Leu
               300                      305                      310

GCC  TCG  CAG  ATC  AAC  CTC  ATC  CTT  CTG  GAA  CGC  CTG  TGG  TAT  GTT  ATG      1373
Ala  Ser  Gln  Ile  Asn  Leu  Ile  Leu  Leu  Glu  Arg  Leu  Trp  Tyr  Val  Met
     315                      320                      325

CTG  GAG  CAG  TTC  CTC  ATG  AAG  TAT  GTG  TGG  AGC  GCC  TCG  GGC  CTG  CTC      1421
Leu  Glu  Gln  Phe  Leu  Met  Lys  Tyr  Val  Trp  Ser  Ala  Ser  Gly  Leu  Leu
330                      335                      340                      345

ATG  GTG  GCT  GTC  CCC  ATC  ATC  ACT  GCC  ACT  GGC  TAC  TCA  GAG  TCA  GAT      1469
Met  Val  Ala  Val  Pro  Ile  Ile  Thr  Ala  Thr  Gly  Tyr  Ser  Glu  Ser  Asp
                    350                      355                           360

GCA  GAG  GCC  GTG  AAG  AAG  GCA  GCC  TTG  GAA  AAG  AAG  GAG  GAG  GAG  CTG      1517
Ala  Glu  Ala  Val  Lys  Lys  Ala  Ala  Leu  Glu  Lys  Lys  Glu  Glu  Glu  Leu
                    365                      370                           375

GTG  AGC  GAG  CGC  ACA  GAA  GCC  TTC  ACT  ATT  GCC  CGC  AAC  CTC  CTG  ACA      1565
Val  Ser  Glu  Arg  Thr  Glu  Ala  Phe  Thr  Ile  Ala  Arg  Asn  Leu  Leu  Thr
          380                      385                      390

GCG  GCT  GCA  GAT  GCC  ATT  GAG  CGG  ATC  ATG  TCG  TCG  TAC  AAG  GAG  GTG      1613
Ala  Ala  Ala  Asp  Ala  Ile  Glu  Arg  Ile  Met  Ser  Ser  Tyr  Lys  Glu  Val
     395                      400                 405

ACG  GAG  CTG  GCT  GGC  TAC  ACA  GCC  CGG  GTG  CAC  GAG  ATG  TTC  CAG  GTA      1661
Thr  Glu  Leu  Ala  Gly  Tyr  Thr  Ala  Arg  Val  His  Glu  Met  Phe  Gln  Val
410                      415                      420                      425

TTT  GAA  GAT  GTT  CAG  CGC  TGT  CAC  TTC  AAG  AGG  CCC  AGG  GAG  CTA  GAG      1709
Phe  Glu  Asp  Val  Gln  Arg  Cys  His  Phe  Lys  Arg  Pro  Arg  Glu  Leu  Glu
                    430                      435                      440

GAC  GCT  CAG  GCG  GGG  TCT  GGG  ACC  ATA  GGC  CGG  TCT  GGT  GTC  CGT  GTG      1757
Asp  Ala  Gln  Ala  Gly  Ser  Gly  Thr  Ile  Gly  Arg  Ser  Gly  Val  Arg  Val
               445                      450                      455

GAG  GGC  CCC  CTG  AAG  ATC  CGA  GGC  CAG  GTG  GTG  GAT  GTG  GAA  CAG  GGG      1805
Glu  Gly  Pro  Leu  Lys  Ile  Arg  Gly  Gln  Val  Val  Asp  Val  Glu  Gln  Gly
          460                      465                      470

ATC  ATC  TGC  GAG  AAC  ATC  CCC  ATC  GTC  ACG  CCC  TCA  GGA  GAG  GTG  GTG      1853
Ile  Ile  Cys  Glu  Asn  Ile  Pro  Ile  Val  Thr  Pro  Ser  Gly  Glu  Val  Val
475                      480                      485
```

-continued

| | | | | | | | | | | | | | | | |
|---|---|---|---|---|---|---|---|---|---|---|---|---|---|---|---|
| GTG | GCC | AGC | CTC | AAC | ATC | AGG | GTG | GAG | GAA | GGC | ATG | CAT | CTG | CTC | ATC | 1901
| Val | Ala | Ser | Leu | Asn | Ile | Arg | Val | Glu | Glu | Gly | Met | His | Leu | Leu | Ile |
| 490 | | | | | 495 | | | | 500 | | | | | | 505 |
| ACA | GGC | CCC | AAT | GGC | TGC | GGC | AAG | AGC | TCC | CTG | TTC | CGG | ATC | CTG | GGT | 1949
| Thr | Gly | Pro | Asn | Gly | Cys | Gly | Lys | Ser | Ser | Leu | Phe | Arg | Ile | Leu | Gly |
| | | | | 510 | | | | | 515 | | | | | 520 | |
| GGG | CTC | TGG | CCC | ACG | TAC | GGT | GGT | GTG | CTC | TAC | AAG | CCC | CCA | CCC | CAG | 1997
| Gly | Leu | Trp | Pro | Thr | Tyr | Gly | Gly | Val | Leu | Tyr | Lys | Pro | Pro | Pro | Gln |
| | | | 525 | | | | | 530 | | | | | 535 | | |
| CGC | ATG | TTC | TAC | ATC | CCG | CAG | AGG | CCC | TAC | ATG | TCT | GTG | GGC | TCC | CTG | 2045
| Arg | Met | Phe | Tyr | Ile | Pro | Gln | Arg | Pro | Tyr | Met | Ser | Val | Gly | Ser | Leu |
| | | 540 | | | | | 545 | | | | | 550 | | | |
| CGT | GAC | CAG | GTG | ATC | TAC | CCG | GAC | TCA | GTG | GAG | GAC | ATG | CAA | AGG | AAG | 2093
| Arg | Asp | Gln | Val | Ile | Tyr | Pro | Asp | Ser | Val | Glu | Asp | Met | Gln | Arg | Lys |
| | 555 | | | | | 560 | | | | | 565 | | | | |
| GGC | TAC | TCG | GAG | CAG | GAC | CTG | GAA | GCC | ATC | CTG | GAC | GTC | GTG | CAC | CTG | 2141
| Gly | Tyr | Ser | Glu | Gln | Asp | Leu | Glu | Ala | Ile | Leu | Asp | Val | Val | His | Leu |
| 570 | | | | | 575 | | | | | 580 | | | | | 585 |
| CAC | CAC | ATC | CTG | CAG | CGG | GAG | GGA | GGT | TGG | GAG | GCT | ATG | TGT | GAC | TGG | 2189
| His | His | Ile | Leu | Gln | Arg | Glu | Gly | Gly | Trp | Glu | Ala | Met | Cys | Asp | Trp |
| | | | | 590 | | | | | 595 | | | | | 600 | |
| AAG | GAC | GTC | CTG | TCG | GGT | GGC | GAG | AAG | CAG | AGA | ATC | GGC | ATG | GCC | CGC | 2237
| Lys | Asp | Val | Leu | Ser | Gly | Gly | Glu | Lys | Gln | Arg | Ile | Gly | Met | Ala | Arg |
| | | | 605 | | | | | 610 | | | | | 615 | | |
| ATG | TTC | TAC | CAC | AGG | CCC | AAG | TAC | GCC | CTC | CTG | GAT | GAA | TGC | ACC | AGC | 2285
| Met | Phe | Tyr | His | Arg | Pro | Lys | Tyr | Ala | Leu | Leu | Asp | Glu | Cys | Thr | Ser |
| | | 620 | | | | | 625 | | | | | 630 | | | |
| GCC | GTG | AGC | ATC | GAC | GTG | GAA | GGC | AAG | ATC | TTC | CAG | GCG | GCC | AAG | GAC | 2333
| Ala | Val | Ser | Ile | Asp | Val | Glu | Gly | Lys | Ile | Phe | Gln | Ala | Ala | Lys | Asp |
| | 635 | | | | | 640 | | | | | 645 | | | | |
| GCG | GGC | ATT | GCC | CTG | CTC | TCC | ATC | ACC | CAC | CGG | CCC | TCC | CTG | TGG | AAA | 2381
| Ala | Gly | Ile | Ala | Leu | Leu | Ser | Ile | Thr | His | Arg | Pro | Ser | Leu | Trp | Lys |
| 650 | | | | | 655 | | | | | 660 | | | | | 665 |
| TAC | CAC | ACA | CAC | TTG | CTA | CAG | TTC | GAT | GGG | GAG | GGC | GGC | TGG | AAG | TTC | 2429
| Tyr | His | Thr | His | Leu | Leu | Gln | Phe | Asp | Gly | Glu | Gly | Gly | Trp | Lys | Phe |
| | | | | 670 | | | | | 675 | | | | | 680 | |
| GAG | AAG | CTG | GAC | TCA | GCT | GCC | CGC | CTG | AGC | CTG | ACG | GAG | GAG | AAG | CAG | 2477
| Glu | Lys | Leu | Asp | Ser | Ala | Ala | Arg | Leu | Ser | Leu | Thr | Glu | Glu | Lys | Gln |
| | | | 685 | | | | | 690 | | | | | 695 | | |
| CGG | CTG | GAG | CAG | CAG | CTG | GCG | GGC | ATT | CCC | AAG | ATG | CAG | CGG | CGC | CTC | 2525
| Arg | Leu | Glu | Gln | Gln | Leu | Ala | Gly | Ile | Pro | Lys | Met | Gln | Arg | Arg | Leu |
| | | 700 | | | | | 705 | | | | | 710 | | | |
| CAG | GAG | CTC | TGC | CAG | ATC | CTG | GGC | GAG | GCC | GTG | GCC | CCA | GCG | CAT | GTG | 2573
| Gln | Glu | Leu | Cys | Gln | Ile | Leu | Gly | Glu | Ala | Val | Ala | Pro | Ala | His | Val |
| | 715 | | | | | 720 | | | | | 725 | | | | |
| CCG | GCA | CCT | AGC | CCG | CAA | GGC | CCT | GGT | GGC | CTC | CAG | GGT | GCC | TCC | ACC | 2621
| Pro | Ala | Pro | Ser | Pro | Gln | Gly | Pro | Gly | Gly | Leu | Gln | Gly | Ala | Ser | Thr |
| 730 | | | | | 735 | | | | | 740 | | | | | 745 |

TGACACAACC GTCCCCGGCC CCTGCCCCGC CCCCAAGCTC GGATCACATG AAGGAGACAG 2681

CAGCACCCAC CCATGCACGC ACCCCGCCCC TGCATGCCTG GCCCCTCCTC CTAGAAAACC 2741

CTTCCCGCC 2750

( 2 ) INFORMATION FOR SEQ ID NO:2:

( i ) SEQUENCE CHARACTERISTICS:
        ( A ) LENGTH: 745 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Pro | Val | Leu | Ser | Arg | Pro | Arg | Pro | Trp | Arg | Gly | Asn | Thr | Leu | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Thr | Ala | Val | Leu | Leu | Ala | Leu | Ala | Ala | Tyr | Gly | Ala | His | Lys | Val |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Tyr | Pro | Leu | Val | Arg | Gln | Cys | Leu | Ala | Pro | Ala | Arg | Gly | Leu | Gln | Ala |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Pro | Ala | Gly | Glu | Pro | Thr | Gln | Glu | Ala | Ser | Gly | Val | Ala | Ala | Ala | Lys |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ala | Gly | Met | Asn | Arg | Val | Phe | Leu | Gln | Arg | Leu | Leu | Trp | Leu | Leu | Arg |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Leu | Leu | Phe | Pro | Arg | Val | Leu | Cys | Arg | Glu | Thr | Gly | Leu | Leu | Ala | Leu |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| His | Ser | Ala | Ala | Leu | Val | Ser | Arg | Thr | Phe | Leu | Ser | Val | Tyr | Val | Ala |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Arg | Leu | Asp | Gly | Arg | Leu | Ala | Arg | Cys | Ile | Ala | Arg | Lys | Asp | Pro | Arg |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Ala | Phe | Gly | Trp | Gln | Leu | Leu | Gln | Trp | Leu | Leu | Ile | Ala | Leu | Pro | Ala |
|-----|-----|-----|-----|-----|-----|-----|-----|-----|-----|-----|-----|-----|-----|-----|-----|
|     |     | 130 |     |     |     |     | 135 |     |     |     |     | 140 |     |     |     |

| Thr | Phe | Val | Asn | Ser | Ala | Ile | Arg | Tyr | Leu | Glu | Gly | Gln | Leu | Ala | Leu |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Ser | Phe | Arg | Ser | Arg | Leu | Val | Ala | His | Ala | Tyr | Arg | Leu | Tyr | Phe | Ser |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Gln | Gln | Thr | Tyr | Tyr | Arg | Val | Ser | Asn | Met | Asp | Gly | Arg | Leu | Arg | Asn |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Pro | Asp | Gln | Ser | Leu | Thr | Glu | Asp | Val | Val | Ala | Phe | Ala | Ala | Ser | Val |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Ala | His | Leu | Tyr | Ser | Asn | Leu | Thr | Lys | Pro | Leu | Leu | Asp | Val | Ala | Val |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Thr | Ser | Tyr | Thr | Leu | Leu | Arg | Ala | Ala | Arg | Ser | Arg | Gly | Ala | Gly | Thr |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Ala | Trp | Pro | Ser | Ala | Ile | Ala | Gly | Leu | Val | Val | Phe | Leu | Thr | Ala | Asn |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Val | Leu | Arg | Ala | Phe | Ser | Pro | Lys | Phe | Gly | Glu | Leu | Val | Ala | Glu | Glu |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Ala | Arg | Arg | Lys | Gly | Glu | Leu | Arg | Tyr | Met | His | Ser | Arg | Val | Val | Ala |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Asn | Ser | Glu | Glu | Ile | Ala | Phe | Tyr | Gly | Gly | His | Glu | Val | Glu | Leu | Ala |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Leu | Leu | Gln | Arg | Ser | Tyr | Gln | Asp | Leu | Ala | Ser | Gln | Ile | Asn | Leu | Ile |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Leu | Leu | Glu | Arg | Leu | Trp | Tyr | Val | Met | Leu | Glu | Gln | Phe | Leu | Met | Lys |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Tyr | Val | Trp | Ser | Ala | Ser | Gly | Leu | Leu | Met | Val | Ala | Val | Pro | Ile | Ile |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| Thr | Ala | Thr | Gly | Tyr | Ser | Glu | Ser | Asp | Ala | Glu | Ala | Val | Lys | Lys | Ala |
|-----|-----|-----|-----|-----|-----|-----|-----|-----|-----|-----|-----|-----|-----|-----|-----|
|     |     | 355 |     |     |     |     | 360 |     |     |     |     | 365 |     |     |     |

| Ala | Leu | Glu | Lys | Lys | Glu | Glu | Glu | Leu | Val | Ser | Glu | Arg | Thr | Glu | Ala |
|-----|-----|-----|-----|-----|-----|-----|-----|-----|-----|-----|-----|-----|-----|-----|-----|
|     | 370 |     |     |     |     | 375 |     |     |     |     | 380 |     |     |     |     |

| Phe | Thr | Ile | Ala | Arg | Asn | Leu | Leu | Thr | Ala | Ala | Ala | Asp | Ala | Ile | Glu |
|-----|-----|-----|-----|-----|-----|-----|-----|-----|-----|-----|-----|-----|-----|-----|-----|
| 385 |     |     |     |     | 390 |     |     |     |     | 395 |     |     |     |     | 400 |

| Arg | Ile | Met | Ser | Ser | Tyr | Lys | Glu | Val | Thr | Glu | Leu | Ala | Gly | Tyr | Thr |
|-----|-----|-----|-----|-----|-----|-----|-----|-----|-----|-----|-----|-----|-----|-----|-----|
|     |     |     |     | 405 |     |     |     |     | 410 |     |     |     |     | 415 |     |

-continued

| | | | | | | | | | | | | | | |
|---|---|---|---|---|---|---|---|---|---|---|---|---|---|---|
| Ala | Arg | Val | His<br>420 | Glu | Met | Phe | Gln<br>425 | Val | Phe | Glu | Asp | Val<br>430 | Gln | Arg | Cys |
| His | Phe | Lys<br>435 | Arg | Pro | Arg | Glu | Leu<br>440 | Glu | Asp | Ala | Gln | Ala<br>445 | Gly | Ser | Gly |
| Thr | Ile<br>450 | Gly | Arg | Ser | Gly | Val<br>455 | Arg | Val | Glu | Gly | Pro<br>460 | Leu | Lys | Ile | Arg |
| Gly<br>465 | Gln | Val | Val | Asp | Val<br>470 | Glu | Gln | Gly | Ile | Ile<br>475 | Cys | Glu | Asn | Ile | Pro<br>480 |
| Ile | Val | Thr | Pro | Ser<br>485 | Gly | Glu | Val | Val | Ala<br>490 | Ser | Leu | Asn | Ile<br>495 | Arg |
| Val | Glu | Glu | Gly<br>500 | Met | His | Leu | Leu | Ile<br>505 | Thr | Gly | Pro | Asn | Gly<br>510 | Cys | Gly |
| Lys | Ser | Ser<br>515 | Leu | Phe | Arg | Ile | Leu<br>520 | Gly | Gly | Leu | Trp | Pro<br>525 | Thr | Tyr | Gly |
| Gly | Val<br>530 | Leu | Tyr | Lys | Pro | Pro<br>535 | Pro | Gln | Arg | Met | Phe<br>540 | Tyr | Ile | Pro | Gln |
| Arg<br>545 | Pro | Tyr | Met | Ser | Val<br>550 | Gly | Ser | Leu | Arg | Asp<br>555 | Gln | Val | Ile | Tyr | Pro<br>560 |
| Asp | Ser | Val | Glu | Asp<br>565 | Met | Gln | Arg | Lys | Gly<br>570 | Tyr | Ser | Glu | Gln | Asp<br>575 | Leu |
| Glu | Ala | Ile | Leu<br>580 | Asp | Val | Val | His | Leu<br>585 | His | Ile | Leu | Gln<br>590 | Arg | Glu |
| Gly | Gly | Trp<br>595 | Glu | Ala | Met | Cys | Asp<br>600 | Trp | Lys | Asp | Val | Leu<br>605 | Ser | Gly | Gly |
| Glu | Lys<br>610 | Gln | Arg | Ile | Gly | Met<br>615 | Ala | Arg | Met | Phe | Tyr<br>620 | His | Arg | Pro | Lys |
| Tyr<br>625 | Ala | Leu | Leu | Asp | Glu<br>630 | Cys | Thr | Ser | Ala | Val<br>635 | Ser | Ile | Asp | Val | Glu<br>640 |
| Gly | Lys | Ile | Phe | Gln<br>645 | Ala | Ala | Lys | Asp | Ala<br>650 | Gly | Ile | Ala | Leu | Leu<br>655 | Ser |
| Ile | Thr | His | Arg<br>660 | Pro | Ser | Leu | Trp | Lys<br>665 | Tyr | His | Thr | His | Leu<br>670 | Leu | Gln |
| Phe | Asp | Gly<br>675 | Glu | Gly | Gly | Trp | Lys<br>680 | Phe | Glu | Lys | Leu | Asp<br>685 | Ser | Ala | Ala |
| Arg | Leu<br>690 | Ser | Leu | Thr | Glu | Glu<br>695 | Lys | Gln | Arg | Leu | Glu<br>700 | Gln | Gln | Leu | Ala |
| Gly<br>705 | Ile | Pro | Lys | Met | Gln<br>710 | Arg | Arg | Leu | Gln | Glu<br>715 | Leu | Cys | Gln | Ile | Leu<br>720 |
| Gly | Glu | Ala | Val | Ala<br>725 | Pro | Ala | His | Val | Pro<br>730 | Ala | Pro | Ser | Pro | Gln<br>735 | Gly |
| Pro | Gly | Gly | Leu<br>740 | Gln | Gly | Ala | Ser | Thr<br>745 |

( 2 ) INFORMATION FOR SEQ ID NO:3:

( i ) SEQUENCE CHARACTERISTICS:
        ( A ) LENGTH: 659 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| | | | | | | | | | | | | | | |
|---|---|---|---|---|---|---|---|---|---|---|---|---|---|---|
| Met<br>1 | Ala | Ala | Phe | Ser<br>5 | Lys | Tyr | Leu | Thr | Ala<br>10 | Arg | Asn | Ser | Ser | Leu<br>15 | Ala |
| Gly | Ala | Ala | Phe<br>20 | Leu | Leu | Leu | Cys<br>25 | Leu | Leu | His | Lys | Arg<br>30 | Arg | Arg | Ala |

```
Leu  Gly  Leu  His  Gly  Lys  Lys  Ser  Gly  Lys  Pro  Pro  Leu  Gln  Asn  Asn
          35                      40                 45

Glu  Lys  Glu  Gly  Lys  Lys  Glu  Arg  Ala  Val  Val  Asp  Lys  Val  Phe  Phe
     50                      55                 60

Ser  Arg  Leu  Ile  Gln  Ile  Leu  Lys  Ile  Met  Val  Pro  Arg  Thr  Phe  Cys
65                       70                 75                           80

Lys  Glu  Thr  Gly  Tyr  Leu  Val  Leu  Ile  Ala  Val  Met  Leu  Val  Ser  Arg
               85                      90                           95

Thr  Tyr  Cys  Asp  Val  Trp  Met  Ile  Gln  Asn  Gly  Thr  Leu  Ile  Glu  Ser
               100                      105                110

Gly  Ile  Ile  Gly  Arg  Ser  Arg  Lys  Asp  Phe  Lys  Arg  Tyr  Leu  Leu  Asn
          115                      120                125

Phe  Ile  Ala  Ala  Met  Pro  Leu  Ile  Ser  Leu  Val  Asn  Asn  Phe  Leu  Lys
     130                      135                     140

Tyr  Gly  Leu  Asn  Glu  Leu  Lys  Leu  Cys  Phe  Arg  Val  Arg  Leu  Thr  Lys
145                      150                     155                          160

Tyr  Leu  Tyr  Glu  Glu  Tyr  Leu  Gln  Ala  Phe  Thr  Tyr  Tyr  Lys  Lys  Gly
               165                      170                          175

Asn  Leu  Asp  Asn  Arg  Ile  Ala  Asn  Pro  Asp  Gln  Leu  Leu  Thr  Gln  Asp
               180                      185                190

Val  Glu  Lys  Phe  Cys  Asn  Ser  Val  Asp  Leu  Tyr  Ser  Asn  Leu  Ser
          195                      200                205

Lys  Pro  Phe  Leu  Asp  Ile  Val  Leu  Tyr  Ile  Phe  Lys  Leu  Thr  Ser  Ala
     210                      215                     220

Ile  Gly  Ala  Gln  Gly  Pro  Ala  Ser  Met  Met  Ala  Tyr  Leu  Val  Val  Ser
225                      230                     235                          240

Gly  Leu  Phe  Leu  Thr  Arg  Leu  Arg  Arg  Pro  Ile  Gly  Lys  Met  Thr  Ile
               245                      250                          255

Thr  Glu  Gln  Lys  Tyr  Glu  Gly  Glu  Tyr  Arg  Tyr  Val  Asn  Ser  Arg  Leu
               260                      265                270

Ile  Thr  Asn  Ser  Glu  Glu  Ile  Ala  Phe  Tyr  Asn  Gly  Asn  Lys  Arg  Glu
          275                      280                285

Lys  Gln  Thr  Val  His  Ser  Val  Phe  Arg  Lys  Leu  Val  Glu  His  Leu  His
     290                      295                     300

Asn  Phe  Ile  Leu  Phe  Arg  Phe  Ser  Met  Gly  Phe  Ile  Asp  Ser  Ile  Ile
305                      310                     315                          320

Ala  Lys  Tyr  Leu  Ala  Thr  Val  Val  Gly  Tyr  Leu  Val  Val  Ser  Arg  Pro
               325                      330                          335

Phe  Leu  Asp  Leu  Ser  His  Pro  Arg  His  Leu  Lys  Ser  Thr  His  Ser  Glu
               340                      345                350

Leu  Leu  Glu  Asp  Tyr  Tyr  Gln  Ser  Gly  Arg  Met  Leu  Leu  Arg  Met  Ser
          355                      360                365

Gln  Ala  Leu  Gly  Arg  Ile  Val  Leu  Ala  Gly  Arg  Glu  Met  Thr  Arg  Leu
     370                      375                     380

Ala  Gly  Phe  Thr  Ala  Arg  Ile  Thr  Glu  Leu  Met  Gln  Val  Leu  Lys  Asp
385                      390                     395                          400

Leu  Asn  His  Gly  Lys  Tyr  Glu  Arg  Thr  Met  Val  Ser  Gln  Gln  Glu  Lys
               405                      410                          415

Gly  Ile  Glu  Gly  Val  Gln  Val  Ile  Pro  Leu  Ile  Pro  Gly  Ala  Gly  Glu
               420                      425                430

Ile  Ile  Ile  Ala  Asp  Asn  Ile  Ile  Lys  Phe  Asp  His  Val  Pro  Leu  Ala
          435                      440                445

Thr  Pro  Asn  Gly  Asp  Val  Leu  Ile  Arg  Asp  Leu  Asn  Phe  Glu  Val  Arg
```

|     | 450 |     |     |     | 455 |     |     |     | 460 |     |     |     |
| --- | --- | --- | --- | --- | --- | --- | --- | --- | --- | --- | --- | --- |

Ser  Gly  Ala  Asn  Val  Leu  Ile  Cys  Gly  Pro  Asn  Gly  Cys  Gly  Lys  Ser
465            470                      475                      480

Ser  Leu  Phe  Arg  Val  Leu  Gly  Glu  Leu  Trp  Pro  Leu  Phe  Gly  Gly  Arg
               485                      490                      495

Leu  Thr  Lys  Pro  Glu  Arg  Arg  Lys  Leu  Phe  Tyr  Val  Pro  Gln  Arg  Pro
               500                      505                      510

Tyr  Met  Thr  Leu  Gly  Thr  Leu  Arg  Asp  Gln  Val  Ile  Tyr  Pro  Asp  Gly
          515                      520                      525

Arg  Glu  Asp  Gln  Lys  Arg  Lys  Gly  Ile  Ser  Asp  Leu  Val  Gln  Lys  Glu
          530                      535                      540

Tyr  Leu  Asp  Asn  Val  Gln  Leu  Gly  His  Ile  Leu  Glu  Arg  Glu  Gly  Gly
545                      550                      555                      560

Trp  Asp  Ser  Val  Gln  Asp  Trp  Met  Asp  Val  Leu  Ser  Gly  Gly  Glu  Lys
                    565                      570                      575

Gln  Arg  Met  Ala  Met  Ala  Arg  Leu  Phe  Tyr  His  Lys  Pro  Gln  Phe  Ala
               580                      585                      590

Ile  Leu  Asp  Glu  Cys  Thr  Ser  Ala  Val  Ser  Val  Asp  Val  Glu  Gly  Tyr
          595                      600                      605

Ile  Tyr  Ser  His  Cys  Arg  Lys  Val  Gly  Ile  Thr  Leu  Phe  Thr  Val  Ser
610                      615                      620

His  Arg  Lys  Ser  Leu  Trp  Lys  His  His  Glu  Tyr  Tyr  Leu  His  Met  Asp
625                      630                      635                      640

Gly  Arg  Gly  Asn  Tyr  Glu  Phe  Lys  Gln  Ile  Thr  Glu  Asp  Thr  Val  Glu
                    645                      650                      655

Phe  Gly  Ser ( 2 ) INFORMATION FOR SEQ ID NO:4:

( i ) SEQUENCE CHARACTERISTICS:
        ( A ) LENGTH: 152 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
AGGTGGGGCA  GGTTGGGGTG  CCGGGCACGG  AGGGAAGCGT  GTGGCAGGGA  GGCCCGGGGG      60
CAGGCAGCCG  TGAGCGGTGG  GGACAGTCTG  GGGCGGGCCG  GGGCTGATGC  CAAAGGTGTG     120
GGCAGGCCAT  GGGAGAGCCG  GGCTGGGGTG  GG                                    152
```

( 2 ) INFORMATION FOR SEQ ID NO:5:

( i ) SEQUENCE CHARACTERISTICS:
        ( A ) LENGTH: 152 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
CACCCAATCG  TAACCTCTGG  CTCTCGGCCT  TCTGATGGCC  ACCATGGCAC  AGCGTGTGTG      60
AGTGGCACTG  GGAGACCCTG  ACCATCGCCC  CCACGGGAGC  TGCCCCTGTG  CATGGCCAGG     120
AAGCCTCTCT  GTGTCTGTCA  CCCCCCGCAG  GT                                    152
```

( 2 ) INFORMATION FOR SEQ ID NO:6:

( i ) SEQUENCE CHARACTERISTICS:
  ( A ) LENGTH: 152 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:6:

| | | | | | | |
|---|---|---|---|---|---|---|
| AGGTGAGACC | CAGGGCTCCA | AGAGGATCCA | GGCCAGGGGC | CTGTCCCCCA | TACCGCTGGG | 60 |
| TGCTGAGCTC | ACGAGGGCCC | AACTCAGCCA | GCCCGCCGCC | CACTTCTGCT | GCCGGGGCCA | 120 |
| CCGAGGCCCT | GCTGCCAGCC | TTGATGCTTT | CA | | | 152 |

( 2 ) INFORMATION FOR SEQ ID NO:7:

( i ) SEQUENCE CHARACTERISTICS:
    ( A ) LENGTH: 152 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

| | | | | | | |
|---|---|---|---|---|---|---|
| GCACATAGAG | AGAAAGAGAG | AGAGAGCTGG | TTGCCCCGGC | ACCATTTGCA | GAAGAGCCTC | 60 |
| GCCTTTCTCT | CCAGCGGCTC | ATTTTTGACT | TTCCGCTGTC | TCTGCCCTGC | CCCTCCCCGC | 120 |
| CCCGCCACCC | ACCCCTCTGG | GGCTTTGCAG | AT | | | 152 |

( 2 ) INFORMATION FOR SEQ ID NO:8:

( i ) SEQUENCE CHARACTERISTICS:
    ( A ) LENGTH: 97 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:8:

| | | | | | | |
|---|---|---|---|---|---|---|
| AGGAGGTACC | CCTGGCCCAG | CCCCACCCTT | GCCATCCTTG | CCATGCTTCT | CTCCCTGCAA | 60 |
| CTGGCAGGGG | CTGAGCCAGG | GTCACCCTCC | CTCAGGT | | | 97 |

( 2 ) INFORMATION FOR SEQ ID NO:9:

( i ) SEQUENCE CHARACTERISTICS:
    ( A ) LENGTH: 152 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

| | | | | | | |
|---|---|---|---|---|---|---|
| AGGTAAGGCT | GTCCCCTCCC | TATGAGTGAC | CCCGCCCCTG | CTGCTGCTGC | AGGTGCTGAC | 60 |
| CTGCTGCCCC | AGCTCCTCCT | ATTCCCGCTC | CCTCACTCAG | GGACCTCCAT | GTGCTTCTGG | 120 |
| CCCATCCCAG | TCCACCCAGG | ACGGGAGGGC | TG | | | 152 |

( 2 ) INFORMATION FOR SEQ ID NO:10:

( i ) SEQUENCE CHARACTERISTICS:
    ( A ) LENGTH: 152 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:10:

| | | | | | |
|---|---|---|---|---|---|
| CTGGACCACA | GGCTGCTGGT | CAGGAACCAG | CTGGCATGCT | GCCAGGGATG | GGAATGAGGG | 60
| CGTGCAGCCA | GGGGCACGCA | GACTCCCCAG | AATGCAGAGG | GGTCGCCACC | ACTCCCTCTC | 120
| CACCCCAGCC | CCGCTGTGCT | GTCTCTGCAG | GC | | | 152

( 2 ) INFORMATION FOR SEQ ID NO:11:

( i ) SEQUENCE CHARACTERISTICS:
        ( A ) LENGTH: 152 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

| | | | | | |
|---|---|---|---|---|---|
| GGGTAGGTCC | AGCGGGGAGG | GCGCCAGCCA | CGCACATATG | CAAGCCTCAG | CCCTTGGCTT | 60
| CCCGCCTGTC | TGTGCTGGCA | ACAGCCATTG | TCCCTAGATG | TACGTGGCAG | GTGGGCCAAG | 120
| GTCAAGGTGA | GAGACCAACG | TGTCTCTGAC | TG | | | 152

( 2 ) INFORMATION FOR SEQ ID NO:12:

( i ) SEQUENCE CHARACTERISTICS:
        ( A ) LENGTH: 152 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

| | | | | | |
|---|---|---|---|---|---|
| TCCCCCAGGC | CCTGCTGTCC | CTTATCAAGA | GATCAAGAAT | GGCCTGCGTG | CTGGCCTCGG | 60
| GCATTGGGAG | CCTCTCAAGG | CTGGTCAGGA | GGCCATAGGG | TACGGAAGG | GGCCTGCGCT | 120
| CTCTGGCGTC | AGCGGCTGTT | GCCCCTGCAG | GT | | | 152

( 2 ) INFORMATION FOR SEQ ID NO:13:

( i ) SEQUENCE CHARACTERISTICS:
        ( A ) LENGTH: 340 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

| | | | | | |
|---|---|---|---|---|---|
| AGGTAAGGAA | GCCCGTGCGC | CTCTCCTCCA | CCTCTTCCTG | CCTGTGCGCT | CACACATGGC | 60
| TTCCTGCAGA | GGCCCAGGAA | GTGGTGAAGA | GTCAGCACCT | CAGGAGAGGA | CACTGAGGCA | 120
| CTGTCCCCAG | AGCCAGAGAC | GGGCTGTGGT | TCCTGCTCCC | TCCAAACCCG | CCCGATCCAC | 180
| TGCCCTGTTT | TGGATCTGTG | TGGGGTGTGT | GCACGGGCGG | CGATGTGAGC | GTGTGGATGC | 240
| GTGTGAGCGT | GGCATGTGGA | CACTGCCTGG | GAGGCGCAGA | GTATCTTGGG | GGAGGCAGAG | 300
| CCGGCCCTTC | CCTCCGTGGA | CACCCAGCTT | TCCCACAGGC | | | 340

( 2 ) INFORMATION FOR SEQ ID NO:14:

( i ) SEQUENCE CHARACTERISTICS:
        ( A ) LENGTH: 152 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:14:

| | | | | | |
|---|---|---|---|---|---|
| AGGTAGGAGG | CCTGGGGCTG | GCAGCCACCC | TTTGTCCCAC | CCTGGCCTCT | CCCTTGGCCT | 60
| CCAGGGAGTG | AAGATTACCT | CAACATCCAG | AGTCTAAAGT | GCCAGGTGCC | ACGGGGCGGG | 120
| GCAGAGGCTG | CTACCAGGGA | GGACCAACAC | CA | | | 152

(2) INFORMATION FOR SEQ ID NO:15:

(i) SEQUENCE CHARACTERISTICS:
(A) LENGTH: 152 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:15:

| | | | | | |
|---|---|---|---|---|---|
| ATGATTAATG | CCTGTCAGAC | AGACAAGGAC | GCAGAGGCAC | AGGGGCCCTG | TCGTCACAGC | 60
| TAGCTCATTC | CCGCAGCTCC | CCCAGCTCCC | CGGCTGGCCC | CCGGGTCTGG | GTGCTGGTGG | 120
| AACTGAGCCA | AGACCATTGC | CCCCGCCTAG | GT | | | 152

(2) INFORMATION FOR SEQ ID NO:16:

(i) SEQUENCE CHARACTERISTICS:
(A) LENGTH: 153 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:16:

| | | | | | |
|---|---|---|---|---|---|
| AGGTGAGCAC | TCCGGACCGG | CAGGCTCCCT | GGGGTCCCCT | GGAAGGGGAA | GTAGCAGCTG | 60
| TGGGGAGGCC | TGGGCTCAGT | GGAGCCTGAG | CCGGGCTGGG | GTGTTGGGCC | CTGGAGGGTG | 120
| CACAGACTCT | CCTCTCGGCC | CGGACCCCCA | GGC | | | 153

(2) INFORMATION FOR SEQ ID NO:17:

(i) SEQUENCE CHARACTERISTICS:
(A) LENGTH: 146 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:17:

| | | | | | |
|---|---|---|---|---|---|
| TGGTAGGTGC | CCTGTCTCCC | TGCCTGGGGT | CGGTGGGAGT | GCCTGCCTGA | GGGGAGGAGG | 60
| TGGCCTGGCG | GGCCCGGCAG | CAGCAGGCGG | CTGTCATCAG | CAGCCCCGT | GCCGTGCCCC | 120
| TGACCCTGTC | CCTCTCCTGG | CCAGGA | | | | 146

(2) INFORMATION FOR SEQ ID NO:18:

(i) SEQUENCE CHARACTERISTICS:
(A) LENGTH: 1441 base pairs
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:18:

| | | | | | |
|---|---|---|---|---|---|
| GCGGAGCGGA | CGGACGCGCC | TGGTGCCCCG | GGGAGGGGCG | CCACCGGGGG | AGGAGGAGGA | 60
| GGAGAAGGTG | GAGAGGAAGA | GACGCCCCCT | CTGCCCGAGA | CCTCTCAAGG | CCCTGACCTC | 120
| AGGGGCCAGG | GCACTGACAG | GACAGGAGAG | CCAAGTTCCT | CCACTTGGGC | TGCCCGAAGA | 180
| GGCCGCGACC | CTGGAGGGCC | CTGAGCCCAC | CGCACCAGGG | GCCCCAGCAC | CACCCCGGGG | 240
| GCCTAAAGCG | ACAGTCTCAG | GGGCCATCGC | AAGGTTTCCA | GTTGCCTAGA | CAACAGGCCC | 300
| AGGGTCAGAG | CAACAATCCT | TCCAGCCACC | TGCCTCAACT | GCTGCCCAG | GCACCAGCCC | 360
| CAGTCCCTAC | GCGGCAGCCA | GCCCAGGTGA | CATGCCGGTG | CTCTCCAGGC | CCCGGCCCTG | 420
| GCGGGGAAC | ACGCTGAAGC | GCACGGCCGT | GCTCCTGGCC | CTCGCGGCCT | ATGGAGCCCA | 480
| CAAAGTCTAC | CCCTTGGTGC | GCCAGTGCCT | GGCCCCGGCC | AGGGGTCTTC | AGGCGCCCGC | 540
| CGGGGAGCCC | ACGCAGGAGG | CCTCCGGGGT | CGCGGCGGCC | AAAGCTGGCA | TGAACCGGGT | 600
| ATTCCTGCAG | CGGCTCCTGT | GGCTCCTGCG | GCTGCTGTTC | CCCCGGGTCC | TGTGCCGGGA | 660
| GACGGGGCTG | CTGGCCCTGC | ACTCGGCCGC | CTTGGTGAGC | CGCACCTTCC | TGTCGGTGTA | 720
| TGTGGCCCGC | CTGGACGGAA | GGCTGGCCCG | CTGCATCGCC | CGCAAGGACC | CGCGGGCTTT | 780
| TGGCTGGCAG | CTGCTGCAGT | GGCTCCTCAT | CGCCCTCCCT | GCTACCTTCG | TCAACAGTGC | 840
| CATCCGTTAC | CTGGAGGGCC | AACTGGCCCT | GTCGTTCCGC | AGCCGTCTGG | TGGCCCACGC | 900
| CTACCGCCTC | TACTTCTCCC | AGCAGACCTA | CTACCGGGTC | AGCAACATGG | ACGGGCGGCT | 960
| TCGCAACCCT | GACCAGTCTC | TGACGGAGGA | CGTGGTGGCC | TTTGCGGCCT | CTGTGGCCCA | 1020
| CCTCTACTCC | AACCTGACCA | AGCCACTCCT | GGACGTGGCT | GTGACTTCCT | ACACCCTGCT | 1080
| TCGGGCGGCC | CGCTCCCGTG | GAGCCGGCAC | AGCCTGGCCC | TCGGCCATCG | CCGGCCTCGT | 1140
| GGTGTTCCTC | ACGGCCAACG | TGCTGCGGGC | CTTCTCGCCC | AAGTTCGGGG | AGCTGGTGGC | 1200
| AGAGGAGGCG | CGGCGGAAGG | GGGAGCTGCG | CTACATGCAC | TCGCGTGTGG | TGGCCAACTC | 1260
| GGAGGAGATC | GCCTTCTATG | GGGGCCATGA | GGTGGGGCAG | GTTGGGGTGC | CGGGCACGGA | 1320
| GGGAAGCGTG | TGGCAGGGAG | GCCCGGGGGC | AGGCAGCCGT | GAGCGGTGGG | GACAGTCTGG | 1380
| GGCGGGCCGG | GGCTGATGCC | AAAGGTGTGG | GCAGGCCATG | GGAGAGCCGG | GCTGGGGTGG | 1440
| G | | | | | | 1441

( 2 ) INFORMATION FOR SEQ ID NO:19:

( i ) SEQUENCE CHARACTERISTICS:
        ( A ) LENGTH: 481 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

| | | | | | |
|---|---|---|---|---|---|
| CACCCAATCG | TAACCTCTGG | CTCTCGGCCT | TCTGATGGCC | ACCATGGCAC | AGCGTGTGTG | 60
| AGTGGCACTG | GGAGACCCTG | ACCATCGCCC | CCACGGGAGC | TGCCCCTGTG | CATGGCCAGG | 120
| AAGCCTCTCT | GTGTCTGTCA | CCCCCCGCAG | GTGGAGCTGG | CCCTGCTACA | GCGCTCCTAC | 180
| CAGGACCTGG | CCTCGCAGAT | CAACCTCATC | CTTCTGGAAC | GCCTGTGGTA | TGTTATGCTG | 240
| GAGCAGTTCC | TCATGAAGTA | TGTGTGGAGC | GCCTCGGGCC | TGCTCATGGT | GGCTGTCCCC | 300
| ATCATCACTG | CCACTGGCTA | CTCAGAGTCA | GGTGAGACCC | AGGGCTCCAA | GAGGATCCAG | 360
| GCCAGGGGCC | TGTCCCCCAT | ACCGCTGGGT | GCTGAGCTCA | CGAGGGCCCA | ACTCAGCCAG | 420

|   |   |   |   |   |   |
|---|---|---|---|---|---|
| CCCGCCGCCC | ACTTCTGCTG | CCGGGGCCAC | CGAGGCCCTG | CTGCCAGCCT | TGATGCTTTC | 480 |
| A | | | | | | 481 |

( 2 ) INFORMATION FOR SEQ ID NO:20:

( i ) SEQUENCE CHARACTERISTICS:
        ( A ) LENGTH: 702 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

|   |   |   |   |   |   |   |
|---|---|---|---|---|---|---|
| GCACATAGAG | AGAAAGAGAG | AGAGAGCTGG | TTGCCCCGGC | ACCATTTGCA | GAAGAGCCTC | 60 |
| GCCTTTCTCT | CCAGCGGCTC | ATTTTTGACT | TTCCGCTGTC | TCTGCCCTGC | CCCTCCCCGC | 120 |
| CCCGCCACCC | ACCCCTCTGG | GGCTTTGCAG | ATGCAGAGGC | CGTGAAGAAG | GCAGCCTTGG | 180 |
| AAAAGAAGGA | GGAGGAGCTG | GTGAGCGAGC | GCACAGAAGC | CTTCACTATT | GCCCGCAACC | 240 |
| TCCTGACAGC | GGCTGCAGAT | GCCATTGAGC | GGATCATGTC | GTCGTACAAG | GAGGTACCCC | 300 |
| TGGCCCAGCC | CCACCCTTGC | CATCCTTGCC | ATGCTTCTCT | CCCTGCAACT | GGCAGGGGCT | 360 |
| GAGCCAGGGT | CACCCTCCCT | CAGGTGACGG | AGCTGGCTGG | CTACACAGCC | CGGGTGCACG | 420 |
| AGATGTTCCA | GGTATTTGAA | GATGTTCAGC | GCTGTCACTT | CAAGAGGCCC | AGGGAGCTAG | 480 |
| AGGACGCTCA | GGCGGGGTCT | GGGACCATAG | GCCGGTCTGG | TGTCCGTGTG | GAGGGCCCCC | 540 |
| TGAAGATCCG | AGGTAAGGCT | GTCCCCTCCC | TATGAGTGAC | CCCGCCCTG | CTGCTGCTGC | 600 |
| AGGTGCTGAC | CTGCTGCCCC | AGCTCCTCCT | ATTCCCGCTC | CCTCACTCAG | GGACCTCCAT | 660 |
| GTGCTTCTGG | CCCATCCCAG | TCCACCCAGG | ACGGGAGGGC | TG | | 702 |

( 2 ) INFORMATION FOR SEQ ID NO:21:

( i ) SEQUENCE CHARACTERISTICS:
        ( A ) LENGTH: 395 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

|   |   |   |   |   |   |   |
|---|---|---|---|---|---|---|
| CTGGACCACA | GGCTGCTGGT | CAGGAACCAG | CTGGCATGCT | GCCAGGGATG | GGAATGAGGG | 60 |
| CGTGCAGCCA | GGGGCACGCA | GACTCCCCAG | AATGCAGAGG | GGTCGCCACC | ACTCCCTCTC | 120 |
| CACCCCAGCC | CCGCTGTGCT | GTCTCTGCAG | GCCAGGTGGT | GGATGTGGAA | CAGGGGATCA | 180 |
| TCTGCGAGAA | CATCCCCATC | GTCACGCCCT | CAGGAGAGGT | GGTGGTGGCC | AGCCTCAACA | 240 |
| TCAGGGTAGG | TCCAGCGGGG | AGGGCGCCAG | CCACGCACAT | ATGCAAGCCT | CAGCCCTTGG | 300 |
| CTTCCCGCCT | GTCTGTGCTG | GCAACAGCCA | TTGTCCCTAG | ATGTACGTGG | CAGGTGGGCC | 360 |
| AAGGTCAAGG | TGAGAGACCA | ACGTGTCTCT | GACTG | | | 395 |

( 2 ) INFORMATION FOR SEQ ID NO:22:

( i ) SEQUENCE CHARACTERISTICS:
        ( A ) LENGTH: 928 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

-continued

| | | | | | | |
|---|---|---|---|---|---|---|
| TCCCCCAGGC | CCTGCTGTCC | CTTATCAAGA | GATCAAGAAT | GGCCTGCGTG | CTGGCCTCGG | 60 |
| GCATTGGGAG | CCTCTCAAGG | CTGGTCAGGA | GGCCATAGGG | TACGGGAAGG | GGCCTGCGCT | 120 |
| CTCTGGCGTC | AGCGGCTGTT | GCCCCTGCAG | GTGGAGGAAG | GCATGCATCT | GCTCATCACA | 180 |
| GGCCCCAATG | GCTGCGGCAA | GAGCTCCCTG | TTCCGGATCC | TGGGTGGGCT | CTGGCCCACG | 240 |
| TACGGTGGTG | TGCTCTACAA | GCCCCCACCC | CAGCGCATGT | TCTACATCCC | GCAGAGGTAA | 300 |
| GGAAGCCCGT | GCGCCTCTCC | TCCACCTCTT | CCTGCCTGTG | CGCTCACACA | TGGCTTCCTG | 360 |
| CAGAGGCCCA | GGAAGTGGTG | AAGAGTCAGC | ACCTCAGGAG | AGGACACTGA | GGCACTGTCC | 420 |
| CCAGAGCCAG | AGACGGGCTG | TGGTTCCTGC | TCCCTCCAAA | CCCGCCCGAT | CCACTGCCCT | 480 |
| GTTTTGGATC | TGTGTGGGGT | GTGTGCACGG | GCGGCGATGT | GAGCGTGTGG | ATGCGTGTGA | 540 |
| GCGTGGCATG | TGGACACTGC | CTGGGAGGCG | CAGAGTATCT | TGGGGGAGGC | AGAGCCGGCC | 600 |
| CTTCCCTCCG | TGGACACCCA | GCTTTCCCAC | AGGCCCTACA | TGTCTGTGGG | CTCCCTGCGT | 660 |
| GACCAGGTGA | TCTACCCGGA | CTCAGTGGAG | GACATGCAAA | GGAAGGGCTA | CTCGGAGCAG | 720 |
| GACCTGGAAG | CCATCCTGGA | CGTCGTGCAC | CTGCACCACA | TCCTGCAGCG | GGAGGGAGGT | 780 |
| AGGAGGCCTG | GGGCTGGCAG | CCACCCTTTG | TCCCACCCTG | GCCTCTCCCT | TGGCCTCCAG | 840 |
| GGAGTGAAGA | TTACCTCAAC | ATCCAGAGTC | TAAAGTGCCA | GGTGCCACGG | GGCGGGGCAG | 900 |
| AGGCTGCTAC | CAGGGAGGAC | CAACACCA | | | | 928 |

( 2 ) INFORMATION FOR SEQ ID NO:23:

( i ) SEQUENCE CHARACTERISTICS:
        ( A ) LENGTH: 1025 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

| | | | | | | |
|---|---|---|---|---|---|---|
| ATGATTAATG | CCTGTCAGAC | AGACAAGGAC | GCAGAGGCAC | AGGGGCCCTG | TCGTCACAGC | 60 |
| TAGCTCATTC | CCGCAGCTCC | CCCAGCTCCC | CGGCTGGCCC | CCGGGTCTGG | GTGCTGGTGG | 120 |
| AACTGAGCCA | AGACCATTGC | CCCCGCCTAG | GTTGGGAGGC | TATGTGTGAC | TGGAAGGACG | 180 |
| TCCTGTCGGG | TGGCGAGAAG | CAGAGAATCG | GCATGGCCCG | CATGTTCTAC | CACAGGTGAG | 240 |
| CACTCCGGAC | CGGCAGGCTC | CCTGGGGTCC | CCTGGAAGGG | GAAGTAGCAG | CTGTGGGGAG | 300 |
| GCCTGGGCTC | AGTGGAGCCT | GAGCCGGGCT | GGGGTGTTGG | GCCCTGGAGG | GTGCACAGAC | 360 |
| TCTCCTCTCG | GCCCGGACCC | CCAGGCCCAA | GTACGCCCTC | CTGGATGAAT | GCACCAGCGC | 420 |
| CGTGAGCATC | GACGTGGAAG | GCAAGATCTT | CCAGGCGGCC | AAGGACGCGG | GCATTGCCCT | 480 |
| GCTCTCCATC | ACCCACCGGC | CCTCCCTGTG | GTAGGTGCCC | TGTCTCCCTG | CCTGGGGTCG | 540 |
| GTGGGAGTGC | CTGCCTGAGG | GGAGGAGGTG | GCCTGGCGGG | CCCGGCAGCA | GCAGGCGGCT | 600 |
| GTCATCAGCA | GCCCCGTGCC | CGTGCCCCTG | ACCCTGTCCC | TCTCCTGGCC | AGGAAATACC | 660 |
| ACACACACTT | GCTACAGTTC | GATGGGGAGG | GCGGCTGGAA | GTTCGAGAAG | CTGGACTCAG | 720 |
| CTGCCCGCCT | GAGCCTGACG | GAGGAGAAGC | AGCGGCTGGA | GCAGCAGCTG | GCGGGCATTC | 780 |
| CCAAGATGCA | GCGGCGCCTC | CAGGAGCTCT | GCCAGATCCT | GGGCGAGGCC | GTGGCCCCAG | 840 |
| CGCATGTGCC | GGCACCTAGC | CCGCAAGGCC | CTGGTGGCCT | CCAGGGTGCC | TCCACCTGAC | 900 |

-continued

| | | | | | | |
|---|---|---|---|---|---|---|
| ACAACCGTCC | CCGGCCCCTG | CCCCGCCCCC | AAGCTCGGAT | CACATGAAGG | AGACAGCAGC | 960 |
| ACCCACCCAT | GCACGCACCC | CGCCCCTGCA | TGCCTGGCCC | CTCCTCCTAG | AAAACCCTTC | 1020 |
| CCGCC | | | | | | 1025 |

We claim:

1. A method for the treatment of adrenoleukodystrophy or adrenomyeloneuropathy, wherein said method comprises administering to a human patient in need of the same an effective amount of hematopoietic cells previously modified by a nucleic acid fragment comprising a sequence as represented on FIG. 2 (SEQ. ID. No:1) or FIG. 6 (SEQ. ID No.:4–17) or FIG. 7 (SEQ. ID. No: 18–23).

2. A method according to claim 1, wherein the hematopoietic cells are stem cells.

3. A method for the somatic transfer to a subject of a nucleic acid fragment, wherein said method comprises the administration to said subject of hematopoietic cells previously modified by said nucleic acid fragment, and wherein said nucleic acid fragment comprises a sequence as represented on FIG. 2 (SEQ. ID No: 1) or FIG. 6 (SEQ. ID. No: 4–17) or FIG. 7 (SEQ. ID No: 18–23).

4. A method according to claim 3, wherein the subject is a human.

5. A method for the treatment of adrenoleukodystrophy or adrenomyeloneuropathy, wherein said method comprises administering to a human patient in need of the same an effective amount of hematopoietic cells modified ex vivo by infection with a retroviral vector containing a nucleic acid fragment comprising a sequence as represented on FIG. 2 (SEQ. ID No: 1) or FIG. 6 (SEQ. ID. No: 4–17) or FIG. 7 (SEQ. ID No: 18–23).

6. A method according to claim 5, wherein the hematopoietic cells are stem cells.

7. A method of treating human hematopoietic cells ex vivo to correct the content of very long chain fatty acids in said hematopoietic cells, comprising:

providing human hematopoietic cells of a patient affected by adrenoleukodystrophy or adrenomyeloneuropathy, and infecting said hematopoietic cells ex vivo with a retroviral vector containing, operably linked to a promoter, a nucleic acid fragment comprising a sequence as represented on FIG. 2 (SEQ. ID No: 1) or FIG. 6 (SEQ. ID. No: 4–17) or FIG. 7 (SEQ. ID No: 18–23), wherein the expression of said nucleic acid in said hematopoietic cells corrects the content of very long chain fatty acids in said hematopoietic cells.

8. A method according to claim 7, wherein the hematopoietic cells are stem cells.

* * * * *